(12) United States Patent
Jonasson et al.

(10) Patent No.: US 11,357,647 B2
(45) Date of Patent: Jun. 14, 2022

(54) PUMP SYSTEM

(71) Applicant: Ossur Iceland ehf, Reykjavik (IS)

(72) Inventors: Hafsteinn Jonasson, Reykjavik (IS); Dadi Granz, Reykjavik (IS); Marco Steinberg, Reykjavik (IS); David Sandahl, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 145 days.

(21) Appl. No.: 16/544,400

(22) Filed: Aug. 19, 2019

(65) Prior Publication Data
US 2019/0365546 A1    Dec. 5, 2019

Related U.S. Application Data

(63) Continuation of application No. 15/236,815, filed on Aug. 15, 2016, now Pat. No. 10,413,429.
(Continued)

(51) Int. Cl.
*A61F 2/66* (2006.01)
*A61F 2/74* (2006.01)
(Continued)

(52) U.S. Cl.
CPC .......... *A61F 2/66* (2013.01); *A61F 2/602* (2013.01); *A61F 2/6607* (2013.01); *A61F 2/74* (2021.08);
(Continued)

(58) Field of Classification Search
CPC ............ A61F 2/602; A61F 2002/501; A61F 2002/5012; A61F 2002/5079;
(Continued)

(56) References Cited

U.S. PATENT DOCUMENTS 708,685 A    9/1902   White
980,457 A    1/1911   Toles
(Continued)

FOREIGN PATENT DOCUMENTS

AU    670631 B2    7/1996
BE    675 386 A    5/1966
(Continued)

OTHER PUBLICATIONS

International Search Report from corresponding PCT Application No. PCT/US2016/033915, dated Jul. 29, 2016.
(Continued)

*Primary Examiner* — David H Willse
(74) *Attorney, Agent, or Firm* — Workman Nydegger

(57) ABSTRACT

A prosthetic system includes a prosthetic foot having an upper foot element with a concave-forward facing portion and foot portion extending forwardly therefrom. An intermediate foot element is disposed below the upper foot element and has a front portion coupled to the foot portion of the upper foot element. A lower foot element is disposed below the intermediate foot element. A pump system is coupled to the prosthetic foot and comprises a pump mechanism including a housing defining a cavity, and a membrane situated in the cavity. The pump mechanism is movable between an original configuration and an expanded configuration. An arm member is connected to the pump mechanism and operatively coupled to the intermediate foot element. The arm member is arranged to move the pump mechanism toward at least the expanded configuration upon movement of the intermediate foot element relative to the upper foot element.

19 Claims, 17 Drawing Sheets

Related U.S. Application Data

(60) Provisional application No. 62/221,752, filed on Sep. 22, 2015, provisional application No. 62/210,561, filed on Aug. 27, 2015.

(51) Int. Cl.
*A61F 2/80* (2006.01)
*A61F 2/60* (2006.01)
*A61F 2/50* (2006.01)

(52) U.S. Cl.
CPC ............... *A61F 2/742* (2021.08); *A61F 2/748* (2021.08); *A61F 2002/501* (2013.01); *A61F 2002/5009* (2013.01); *A61F 2002/5021* (2013.01); *A61F 2002/5079* (2013.01); *A61F 2002/6614* (2013.01); *A61F 2002/6657* (2013.01); *A61F 2002/6664* (2013.01); *A61F 2002/6671* (2013.01); *A61F 2002/6678* (2013.01); *A61F 2002/807* (2013.01)

(58) Field of Classification Search
CPC ........ A61F 2002/6664; A61F 2002/742; A61F 2002/807; A61F 2/742
See application file for complete search history.

(56) References Cited

U.S. PATENT DOCUMENTS

| | | |
|---|---|---|
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,947,156 A | 3/1976 | Becker |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,885,509 A | 3/1999 | Kristinsson |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,136,039 A | 8/2000 | Kristinsson et al. |
| 6,117,117 A | 9/2000 | Mauch |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |

(56) References Cited

U.S. PATENT DOCUMENTS

| | | |
|---|---|---|
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,001,563 B2 | 2/2006 | Janusson et al. |
| 7,025,792 B2 | 4/2006 | Collier |
| 7,025,793 B2 | 4/2006 | Egilsson |
| 7,105,122 B2 | 9/2006 | Karason |
| 7,118,602 B2 | 10/2006 | Bjarnason |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2 | 12/2008 | Collier |
| 7,686,848 B2 | 3/2010 | Christensen |
| 7,744,653 B2 | 6/2010 | Rush et al. |
| 7,896,927 B2 | 3/2011 | Clausen et al. |
| 7,909,884 B2 | 3/2011 | Egilsson et al. |
| 7,922,775 B2 | 4/2011 | Caspers |
| 7,947,085 B2 | 5/2011 | Haines et al. |
| 7,993,413 B2 | 8/2011 | Perkins et al. |
| 8,007,543 B2 | 8/2011 | Martin |
| 8,034,120 B2 | 10/2011 | Egilsson et al. |
| 8,052,760 B2 | 11/2011 | Egilsson et al. |
| 8,080,065 B2 | 12/2011 | Scussel et al. |
| 8,097,043 B2 | 1/2012 | Egilsson |
| 8,097,766 B2 | 1/2012 | Carlson et al. |
| 8,114,167 B2 | 2/2012 | Caspers |
| 8,298,294 B2 | 10/2012 | Kaltenborn et al. |
| 8,317,876 B2 | 11/2012 | Mosler |
| 8,343,233 B2 | 1/2013 | Perkins et al. |
| 8,523,951 B2 | 9/2013 | Kania |
| 8,894,719 B2 | 11/2014 | Egilsson et al. |
| 8,956,422 B2 | 2/2015 | Halldorsson |
| 8,961,618 B2 | 2/2015 | Lecomte et al. |
| 9,044,348 B2 | 6/2015 | Halldorsson et al. |
| 9,072,617 B2 | 7/2015 | Halldorsson et al. |
| 9,198,780 B2 | 12/2015 | Jonsson et al. |
| 9,259,332 B2 | 2/2016 | Danzig et al. |
| 9,364,348 B2 | 6/2016 | Sandahl |
| 9,486,335 B2 | 11/2016 | Halldorsson et al. |
| 9,615,946 B2 | 4/2017 | Halldorsson et al. |
| 9,757,256 B2 | 9/2017 | Sandahl |
| 9,820,873 B2 | 11/2017 | Sandahl |
| 9,889,025 B2 | 2/2018 | Jonsson et al. |
| 9,943,421 B2 | 4/2018 | Sverrisson et al. |
| 2001/0005798 A1 | 6/2001 | Caspers |
| 2001/0016781 A1 | 8/2001 | Caspers |
| 2002/0052663 A1 | 5/2002 | Herr et al. |
| 2002/0087215 A1 | 7/2002 | Caspers |
| 2002/0091449 A1 | 7/2002 | Caspers et al. |
| 2002/0103545 A1 | 8/2002 | Arbogast et al. |
| 2002/0128580 A1 | 9/2002 | Carlson et al. |
| 2003/0191539 A1 | 10/2003 | Caspers |
| 2004/0024322 A1 | 2/2004 | Caspers |
| 2004/0030411 A1 | 2/2004 | Caspers |
| 2004/0049290 A1 | 3/2004 | Bedard |
| 2004/0064195 A1 | 4/2004 | Herr |
| 2004/0122528 A1 | 6/2004 | Egilsson |
| 2004/0163278 A1 | 8/2004 | Caspers et al. |
| 2004/0181290 A1 | 9/2004 | Caspers |
| 2004/0236434 A1 | 11/2004 | Carstens |
| 2004/0260403 A1 | 12/2004 | Patterson et al. |
| 2005/0131324 A1 | 6/2005 | Bledsoe |
| 2005/0131549 A1 | 6/2005 | Caspers |
| 2005/0143838 A1 | 6/2005 | Collier |
| 2005/0240282 A1 | 10/2005 | Rush et al. |
| 2005/0267603 A1 | 12/2005 | Lecomte et al. |
| 2006/0074493 A1 | 4/2006 | Bisbee, III et al. |
| 2006/0212130 A1 | 9/2006 | Collier |
| 2006/0212131 A1 | 9/2006 | Curtis |
| 2006/0224246 A1 | 10/2006 | Clausen et al. |
| 2007/0005149 A1 | 1/2007 | Egilsson et al. |
| 2007/0043316 A1 | 2/2007 | Carlson et al. |
| 2007/0050044 A1 | 3/2007 | Haynes et al. |
| 2007/0055383 A1 | 3/2007 | King |
| 2007/0112440 A1 | 5/2007 | Perkins et al. |
| 2007/0196222 A1 | 8/2007 | Mosler et al. |
| 2007/0204487 A1 | 9/2007 | Clough |
| 2007/0213839 A1 | 9/2007 | Nachbar |
| 2008/0086218 A1 | 4/2008 | Egilsson |
| 2008/0147202 A1 | 6/2008 | Danzig et al. |
| 2008/0147204 A1 | 6/2008 | Ezenwa |
| 2008/0243266 A1 | 10/2008 | Haynes et al. |
| 2008/0269911 A1 | 10/2008 | Street et al. |
| 2008/0269912 A1 | 10/2008 | Gobbers et al. |
| 2009/0036998 A1 | 2/2009 | Finlinson et al. |
| 2009/0132056 A1 | 5/2009 | Kania |
| 2009/0157196 A1 | 6/2009 | Danzig et al. |
| 2009/0198346 A1 | 8/2009 | Perkins et al. |
| 2009/0204229 A1 | 8/2009 | Mosler et al. |
| 2009/0281637 A1 | 11/2009 | Martin |
| 2010/0070051 A1 | 3/2010 | Carstens |
| 2010/0087931 A1 | 4/2010 | Bogue |
| 2010/0106260 A1 | 4/2010 | Phillips |
| 2010/0262261 A1 | 10/2010 | Laghi |
| 2010/0312359 A1 | 12/2010 | Caspers |
| 2010/0312360 A1 | 12/2010 | Caspers |
| 2010/0331749 A1 | 12/2010 | Powaser |
| 2011/0035027 A1 | 2/2011 | McCarthy |
| 2011/0046748 A1 | 2/2011 | Martin et al. |
| 2011/0060421 A1 | 3/2011 | Martin et al. |
| 2011/0071649 A1 | 3/2011 | McKinney |
| 2011/0087142 A1 | 4/2011 | Ravikumar et al. |
| 2011/0125291 A1 | 5/2011 | Tompkins et al. |
| 2011/0130846 A1 | 6/2011 | Kampas et al. |
| 2011/0184532 A1 | 7/2011 | Tompkins |
| 2011/0202143 A1 | 8/2011 | Caspers |
| 2011/0270413 A1 | 11/2011 | Haynes |
| 2011/0295386 A1 | 12/2011 | Perkins et al. |
| 2012/0000092 A1 | 1/2012 | Ingvarsson et al. |
| 2012/0022667 A1 | 1/2012 | Accinni et al. |
| 2012/0035520 A1 | 2/2012 | Ingimudarson et al. |
| 2012/0123559 A1 | 5/2012 | Mosler et al. |
| 2012/0173000 A1 | 7/2012 | Caspers |
| 2012/0173001 A1 | 7/2012 | Caspers |
| 2012/0191217 A1 | 7/2012 | Mackenzie |
| 2013/0053982 A1 | 2/2013 | Halldorsson |
| 2013/0096694 A1 | 4/2013 | Caldwell et al. |
| 2013/0282142 A1 | 10/2013 | Perkins et al. |
| 2013/0289741 A1 | 10/2013 | Halldorsson et al. |
| 2014/0243997 A1 | 8/2014 | Clausen et al. |
| 2014/0249648 A1 | 9/2014 | Sandahl |
| 2016/0120665 A1 | 5/2016 | Muller |
| 2016/0199202 A1 | 7/2016 | Jonasson et al. |
| 2016/0346100 A1 | 12/2016 | Sverrisson et al. |
| 2017/0181871 A1 | 6/2017 | Halldorsson et al. |
| 2018/0008436 A1 | 1/2018 | Sandahl |
| 2018/0055659 A1 | 3/2018 | Sandahl et al. |

FOREIGN PATENT DOCUMENTS

| | | | |
|---|---|---|---|
| CA | 2 098 945 C | 7/1997 | |
| CN | 1946358 A | 4/2007 | |
| CN | 1989342 A | 6/2007 | |
| CN | 101815870 A | 8/2010 | |
| DE | 685 861 | * 12/1939 | ............... A61F 2/66 |
| DE | 685 861 C | 12/1939 | |
| DE | 745 981 C | 5/1944 | |
| DE | 27 12 342 A1 | 9/1977 | |
| DE | 27 29 800 A1 | 1/1979 | |
| DE | 32 21 920 A1 | 4/1983 | |
| DE | 42 17 877 A1 | 12/1992 | |

(56) References Cited

FOREIGN PATENT DOCUMENTS

| | | |
|---|---|---|
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |
| EP | 0 870 485 A2 | 10/1998 |
| EP | 1 875 881 A1 | 1/2008 |
| EP | 2816978 A1 | 12/2014 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | H07-155343 A | 6/1995 |
| RU | 1771722 A1 | 10/1992 |
| RU | 1812982 A3 | 4/1993 |
| RU | 1821177 A1 | 6/1993 |
| WO | 84/00881 A1 | 3/1984 |
| WO | 95/05792 A1 | 3/1995 |
| WO | 96/21405 A1 | 7/1996 |
| WO | 98/04218 A1 | 2/1998 |
| WO | 98/55055 A1 | 12/1998 |
| WO | 99/05991 A2 | 2/1999 |
| WO | 99/65434 A1 | 12/1999 |
| WO | 00/03665 A1 | 1/2000 |
| WO | 00/74611 A2 | 12/2000 |
| WO | 01/54631 A1 | 8/2001 |
| WO | 01/70147 A2 | 9/2001 |
| WO | 02/26158 A2 | 4/2002 |
| WO | 02/065958 A2 | 8/2002 |
| WO | 02/067825 A2 | 9/2002 |
| WO | 02/080813 A2 | 10/2002 |
| WO | 03/077797 A2 | 9/2003 |
| WO | 03/099173 A1 | 12/2003 |
| WO | 03/099188 A1 | 12/2003 |
| WO | 2005/039444 A2 | 5/2005 |
| WO | 2005/105000 A1 | 11/2005 |
| WO | 2009149412 A1 | 12/2009 |
| WO | 2010/141960 A2 | 12/2010 |
| WO | 2011/035099 A1 | 3/2011 |
| WO | 2012010309 A1 | 1/2012 |
| WO | 2014126554 A1 | 8/2014 |
| WO | 2014194998 A1 | 12/2014 |
| WO | 2016112030 A1 | 7/2016 |

OTHER PUBLICATIONS

International Search Report and Written Opinion from PCT Application No. PCT/US2017/048354, dated Nov. 16, 2017.
Office Action from corresponding EP Application No. 16727097.4, dated Sep. 7, 2020.
International Search Report from PCT Application No. PCT/US2015/044434, dated Oct. 8, 2015.
International Search Report from PCT Application No. PCT/US2015/041089, dated Oct. 5, 2015.
International Search Report form PCT Application No. PCT/US2016/012215, dated May 23, 2016.
Brochure, "Sometimes Less is More, Harmony P3 Otto Bock, 12 pages. Available at, http://www.ottobock.com/cps/rde/xbcr/ob_es/646A303-EN-01-1001w.pdf", dated 2012.
Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.
Brochure,"Harmony Certification Course Manual, Original Harmony Pump, 42 pages. Availiable at, http://academy.ottobockus.com/videos/harmony/data/downloads/harmony%20course%20manual%202013.pdf." Dated 2013.
Brochure, Harmony P2 & HD, 2 pages. Available at http://www.ottobock.com/cps/rde/xchg/ob_us_en/hs.xsl/14904.html?id=4641. Dated 2012.
International Search Report from corresponding International PCT Application No. PCT/US2013/025849, dated Jun. 4, 2013.
International Search Report and Written Opinion from corresponding International PCT Application No. PCT/US2013/038668, dated Aug. 7, 2013.
Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.
International Search Report and Written Opinion from corresponding International PCT Application No. PCT/US2014/019218, dated May 9, 2014.

* cited by examiner

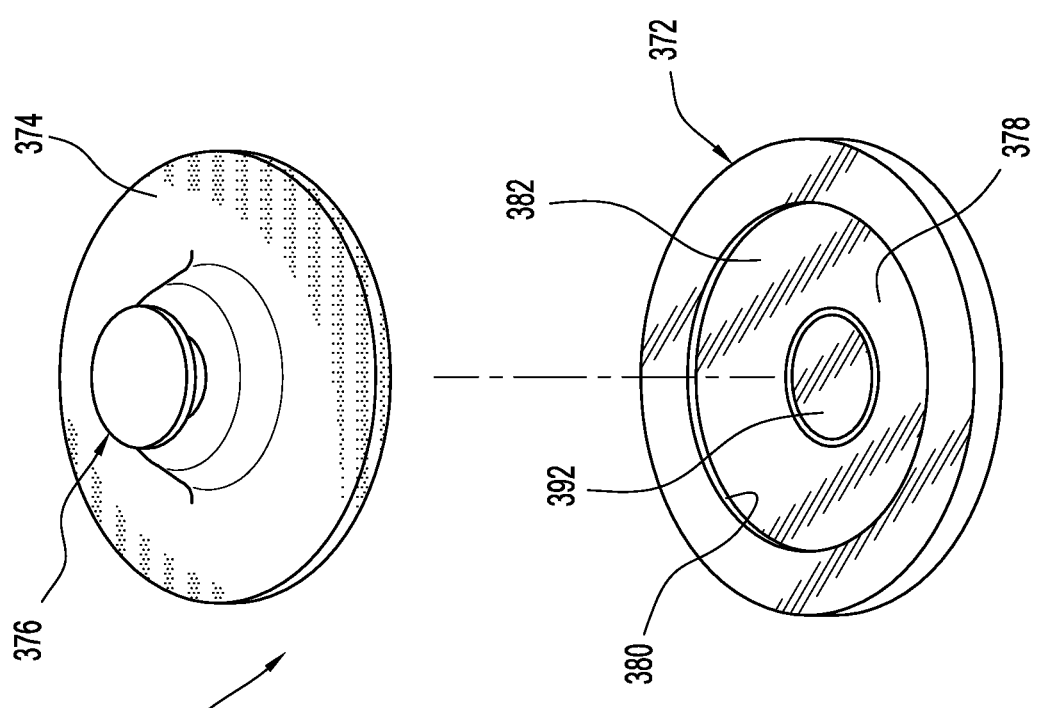
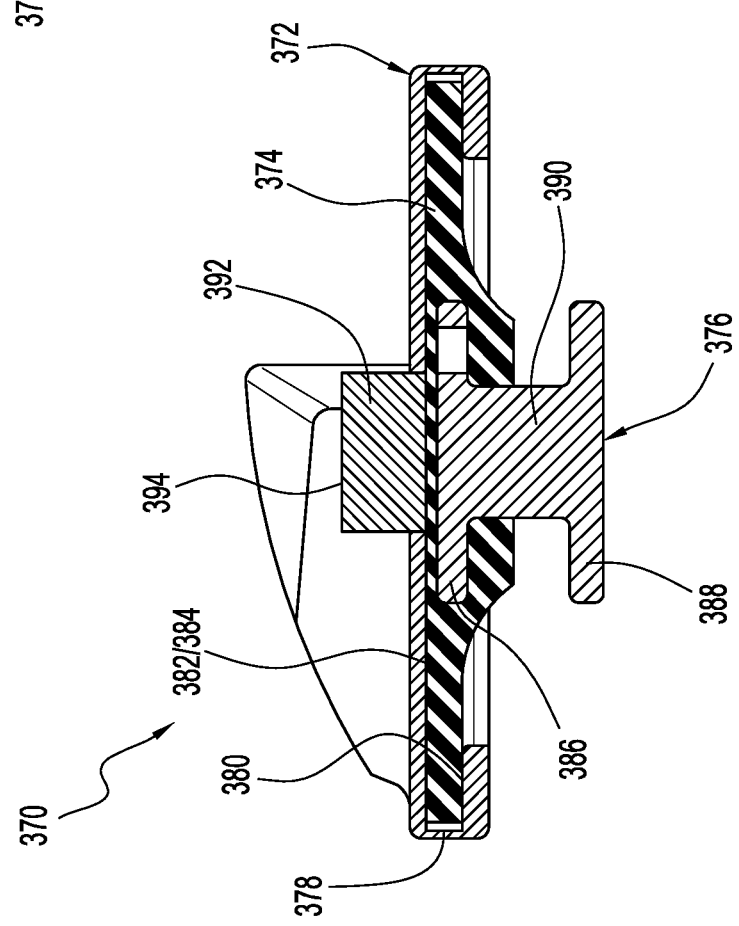
FIG. 20
FIG. 19

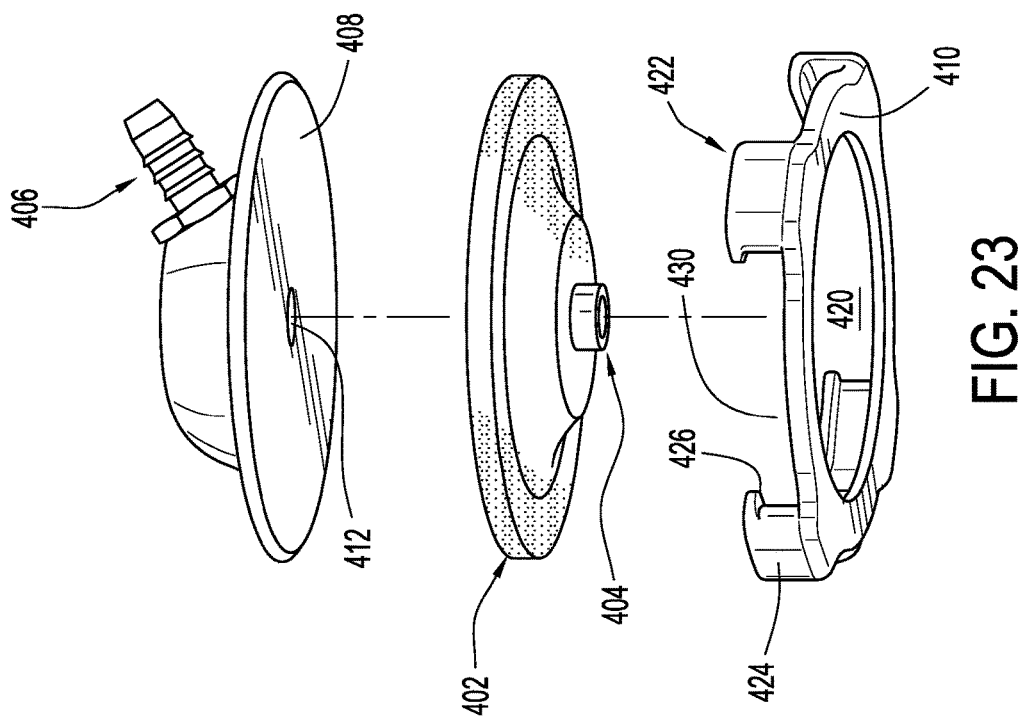
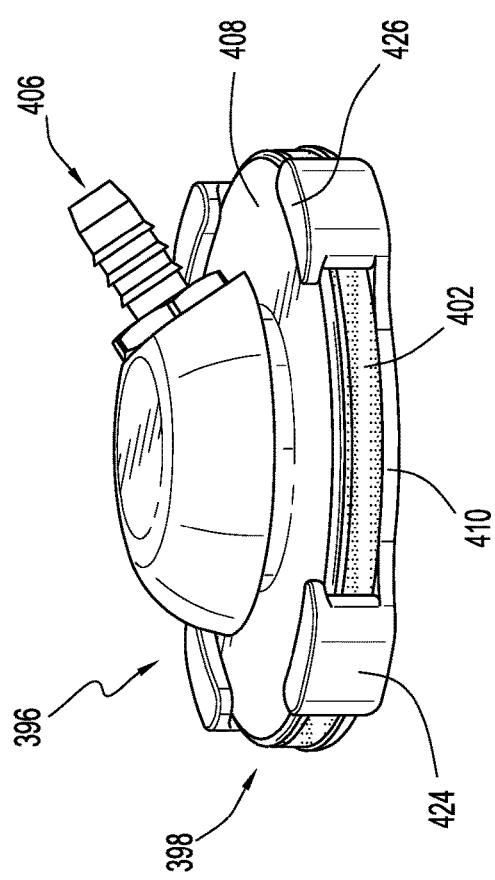
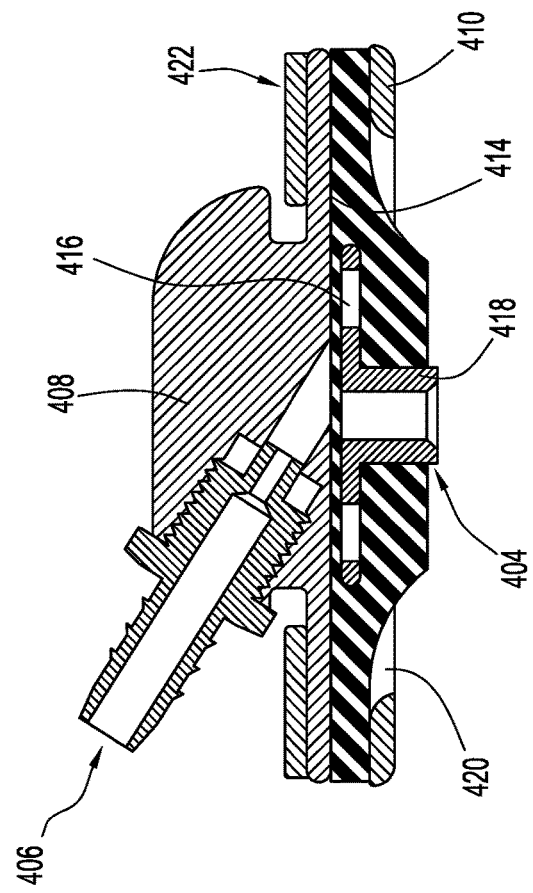

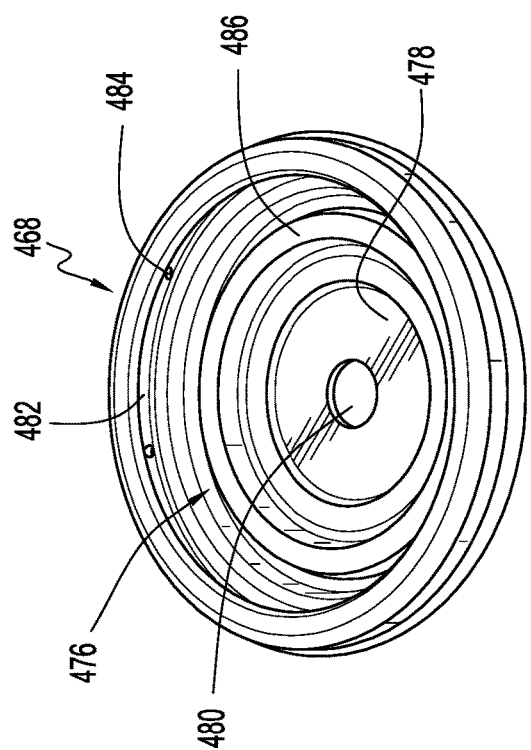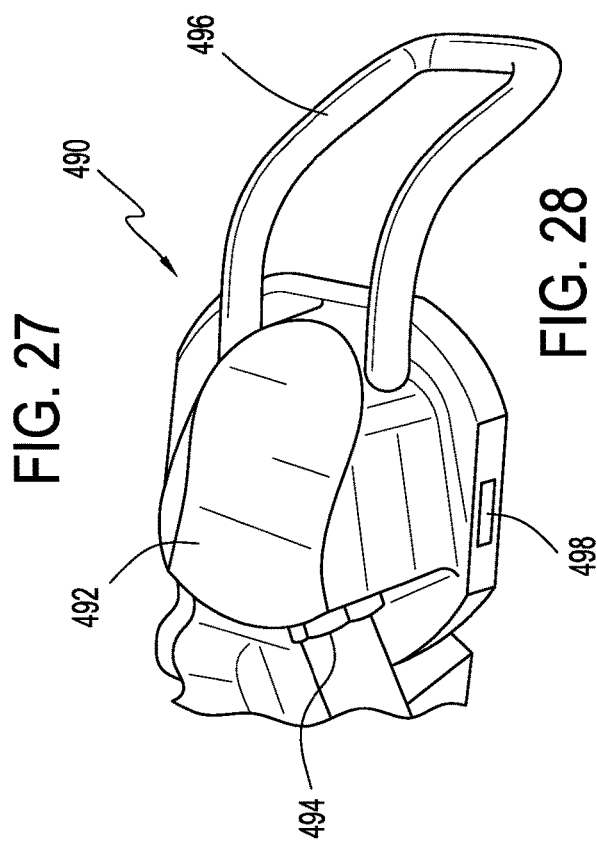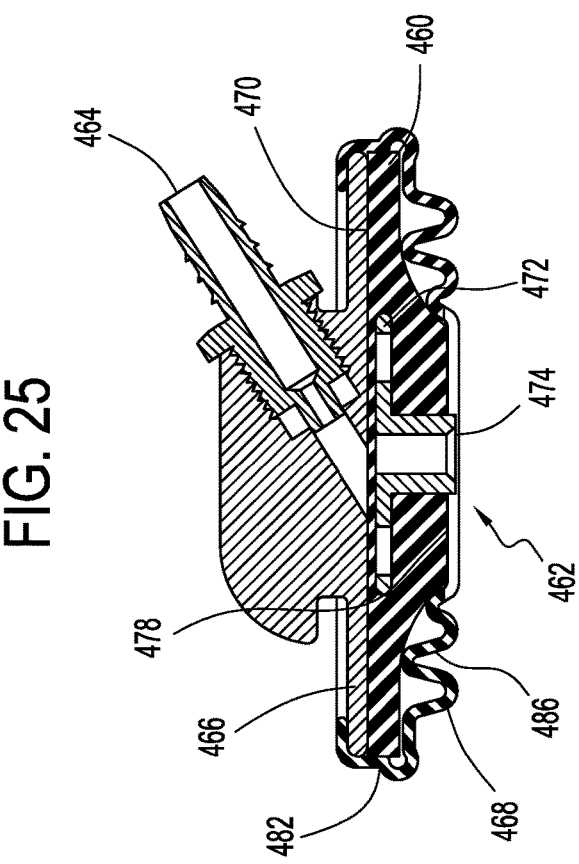

PUMP SYSTEM

TECHNICAL FIELD

The disclosure relates to the field of prosthetic devices, and more particularly to a prosthetic device, system and pump mechanism for increasing vacuum in a vacuum assisted suspension system.

BACKGROUND

An ongoing challenge in the development of prosthetic devices is the attachment of the prosthetic device to the residual limb of a user. For prosthetic legs, it is often difficult to securely attach the prosthetic leg to the residual leg without exerting too much or uneven pressure on the residual limb. On the one hand, the lack of a secure attachment can adversely affect the user's ability to walk. On the other hand, an improper fit can cause sores, swelling and pain for the user.

One approach for overcoming this challenge has been the application of a negative pressure vacuum in a space between the limb (or a liner donned on the limb) and a socket or receptacle coupled to the prosthetic limb. Two conventional ways to apply such a vacuum are by a mechanical pump or an electronic pump.

Mechanical pumps are often in-line systems that utilize the movement of the user to generate the negative pressure vacuum in the socket. For example, the force generated by contacting the ground during a user's walking motion can be used to generate a vacuum in the socket space to hold the prosthesis to the user's limb. However, in utilizing the motion of the user, known pumps rely on complete compression of the pump to expel air from the pump before the pump can be decompressed to generate the vacuum. Because the impact and displacement of the pump is not consistent and varies between users, the vacuum and thus attachment between the residual limb and the socket can be unpredictable and/or inadequate, causing the user discomfort, grief and even injury.

Yet another drawback is that many known pumps are integrated into the prosthetic limb in such a way that any failure of the pump would greatly impair the user's ability to walk. Many of these pumps are also bulky and significantly contribute to the weight of the prosthetic limb, imposing a significant weight burden on the user when walking.

There is a need for a prosthetic device, system, and pump mechanism that provides freedom of vacuum suspension for a prosthetic system. There is also a call for a prosthetic device that provides a secure vacuum without losing suction and confidence to the user over a period of use. It is also desirable for prosthetic devices to draw a vacuum while being lightweight and streamlined.

SUMMARY

Embodiments of the prosthetic system provide vacuum assisted suspension by generating negative pressure inside a prosthetic socket worn over a residual limb, and reducing sliding movement between the liner and the socket. The function of the embodiments is automatic as it is activated during gait. The weight placed on the foot member of the prosthetic foot expands and compresses the foot member, which, in turn, expands a pump mechanism that efficiently draws air out from the socket in each step, and expels it into the atmosphere during swing phase as the pump mechanism returns to an original configuration.

The pump mechanism utilizes the action of the prosthetic foot to create negative pressure inside the socket without substantially affecting the functionality of the prosthetic foot. It also does so without the use of complicated and bulky components as in the prior art, resulting in more secure and reliable elevated vacuum suspension. Furthermore, the pump mechanism can be a separate add-on module to the prosthetic foot and can be adapted to fit a number of different prosthetic feet, providing versatility.

According to an embodiment, the prosthetic system includes a prosthetic foot having an upper foot element with a concave-forward facing portion and foot portion extending forwardly therefrom. An intermediate foot element is disposed below the upper foot element and has a front portion coupled to the foot portion of the upper foot element. A lower foot element is disposed below the intermediate foot element. A pump system is coupled to the prosthetic foot and includes a pump mechanism including a housing defining a cavity, and a membrane situated in the cavity. The pump mechanism is movable between an original configuration in which the volume of a fluid chamber defined between the membrane and the bottom of the cavity is zero or near-zero, and an expanded configuration in which the volume of the fluid chamber is increased. An arm member is connected to the pump mechanism and operatively coupled to the intermediate foot element.

Relative movement between the upper foot element and the intermediate foot element can shift the pump mechanism between the original and expanded configurations. For instance, as the prosthetic foot moves through mid-stance and/or toe-off, the intermediate foot element can move toward the upper foot element, causing the intermediate foot element to apply an upward force on the arm member. This upward force on the arm member forces the arm member and at least a portion of the housing upwardly, pulling the membrane away from the housing and driving the pump mechanism toward the expanded configuration.

The increase in volume of the fluid chamber creates a vacuum in the pump mechanism. Movement of the intermediate foot element toward the upper foot element thus automatically creates a vacuum in the pump mechanism without the use of fixed frame components that add detrimental weight and bulk to the prosthetic foot as in the prior art. It can also do so without engaging the heel of the prosthetic foot, increasing its versatility.

At the end of the stance phase or when the weight of the user is removed from the prosthetic foot, the prosthetic foot returns to its resting position. The inherent properties of the material of the pump mechanism can help move the pump mechanism back toward its original configuration, decreasing the volume of the fluid chamber to a zero or near-zero volume. During the return of the membrane toward the housing, the pump mechanism expels fluid in the fluid chamber out of the pump mechanism. Because the pump mechanism returns to its original configuration of zero or near-zero volume in the fluid chamber at the beginning or end of each gait cycle, all fluid drawn into the pump mechanism is automatically expelled.

According to a variation, the arm member is defined by the housing and is selectively engageable with an upper surface of the intermediate foot element. The arm member can comprise an elongate member having a rigid configuration that extends downwardly from the housing through an opening defined in the upper foot element toward the intermediate foot element. This advantageously helps the prosthetic system maintain a low-profile configuration because the arm member is routed through the prosthetic foot rather than around the prosthetic foot. It also beneficially helps protect the arm member from inadvertent contact with external objects because a length of the arm member is entirely surrounded by the upper foot element, increasing the durability of the pump system.

According to a variation, the arm member defines a width or cross-sectional area increasing in a direction toward the intermediate foot element, providing a more solid connection between the arm member and the intermediate foot element.

BRIEF DESCRIPTION OF THE DRAWINGS

These and other features, aspects, and advantages of the present disclosure will become better understood regarding the following description, appended claims, and accompanying drawings.

FIG. 19 shows a cross section view of a pump mechanism according to another embodiment.

FIG. 20 shows a partial exploded view of the pump mechanism in FIG. 19.

FIG. 21 shows a pump mechanism according to another embodiment.

FIG. 22 shows a cross section view of the pump mechanism in FIG. 21.

FIG. 23 shows a partial exploded view of the pump mechanism in FIG. 21.

FIG. 25 shows a pump mechanism according to another embodiment.

FIG. 26 shows a cross section view of the pump mechanism in FIG. 25.

FIG. 27 shows the base member in FIG. 25 removed from the pump mechanism.

FIG. 28 shows a partial view of a pump mechanism according to another embodiment.

DETAILED DESCRIPTION OF THE DISCLOSURE

Figure 1:
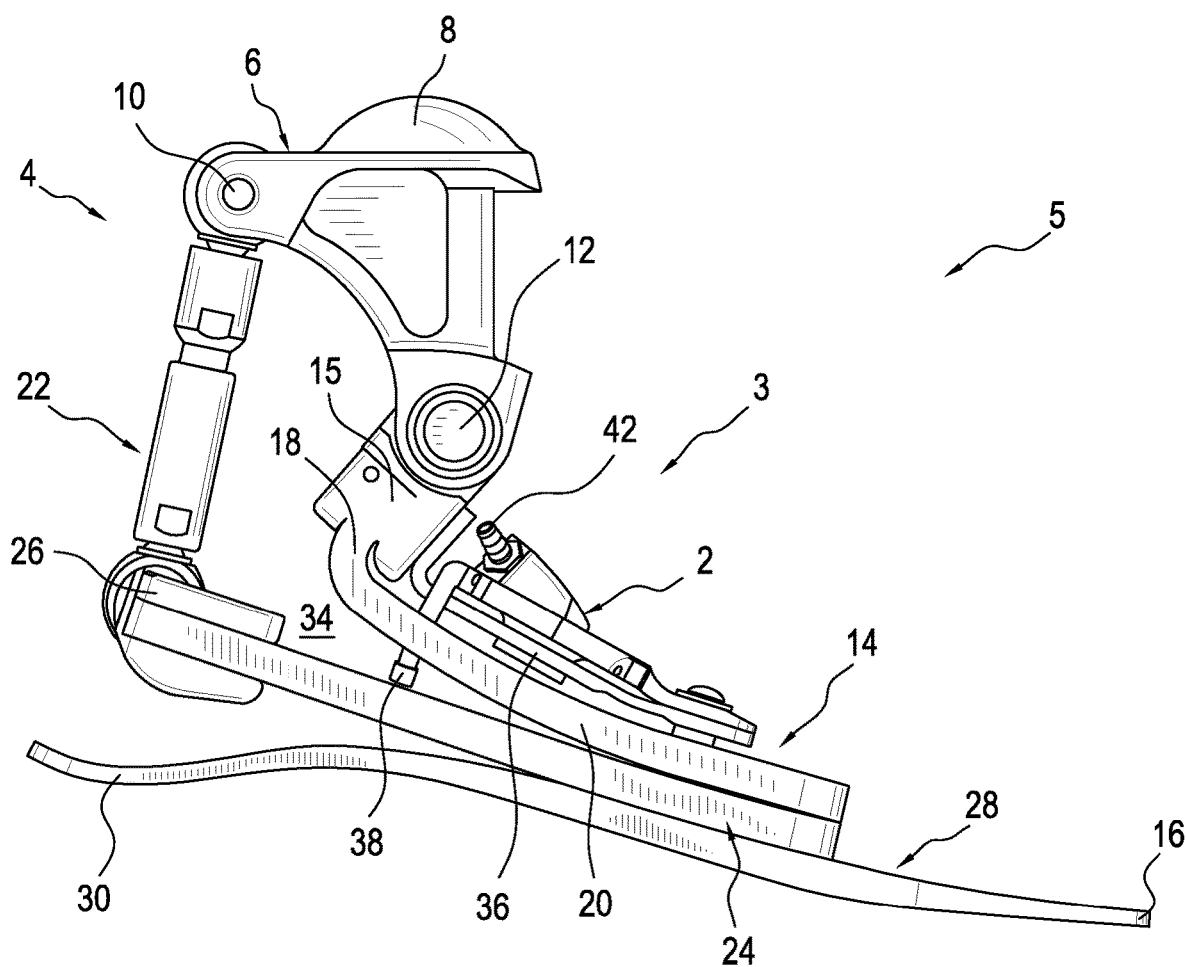
FIG. 1 shows a prosthetic system with a pump system according to an embodiment.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

The embodiments of a prosthetic system will be described which form part of a vacuum system. A vacuum pump mechanism having a fluid connection with a socket assists in creating a vacuum between a residual limb and the socket by pumping fluid out of the socket. The fluid is pumped out of the socket when the user puts his weight on a prosthetic foot such as upon heel strike, mid-stance and/or toe-off. The user's weight on the prosthetic foot can cause the pump mechanism to increase the volume of a fluid chamber in the pump mechanism. The increase in volume of the pump mechanism draws in fluid from the vacuum space between the residual limb and the socket of a prosthetic limb. In this manner, the pump mechanism decreases the air pressure within the vacuum space causing a vacuum effect.

After the weight is removed, and/or shifted on the prosthetic foot, the volume of the fluid chamber in the pump mechanism is automatically decreased. The connection between the vacuum space and the pump may have a one-way valve assembly, so all of the air within the volume of the pump is expelled out of an outlet to another space or to atmosphere. The outlet can be provided with a one-way valve assembly so the vacuum space is the only source of air.

The vacuum suspension system of the present disclosure produces a vacuum effect in a prosthetic socket that is advantageous over prior art devices that require compression of the pump to expel air before the pump can be decompressed to draw in air. The present disclosure also achieves smaller fluctuations in air pressure than the prior art systems, so the difference between the greatest pressure and lowest pressure in the vacuum space of the socket is less.

The efficiency of the pump mechanism is determined at least in part by how effectively the volume of the fluid chamber is reduced. Since the pump mechanism begins at and returns to the original state of zero or near-zero volume at the beginning or end of each cycle in some embodiments, the volume of the fluid chamber is determined by the force applied to the pump, not by a full compression and recompression cycle as in the prior art. In addition, all fluid drawn into the pump mechanism is expelled afterwards, fully utilizing the volume of the fluid chamber.

The vacuum suspension system also reduces volume fluctuations of the residual limb and allows for increased proprioception and reduced pistoning since there is a better attachment between the socket and the residual limb. It may also be beneficial to produce hypobaric pressure below a certain level in the socket. This may be achieved using a sealing membrane or seal component between the residual limb and the socket, instead of the conventional sealing method of using a sleeve to form an airtight connection between the residual limb and the proximal end of the socket. The sealing membrane may be on a prosthetic liner as described in U.S. Pat. No. 8,034,120 incorporated by reference and belonging to the assignee of this disclosure.

The benefit of using a liner having a seal or seal component reduces the volume of air to be drawn out of the socket and therefore, a better suspension may be achieved in a shorter time period. Using a silicone liner with integrated seal also provides the added benefit that the hypobaric region is not directly applied to the skin.

The vacuum pump mechanisms in the embodiments of the prosthetic system described are generally described as a pump mechanism and may include any suitable type of pump mechanism. For instance, the pump mechanism may be a pump as described in U.S. patent application Ser. No. 14/747,788 incorporated by reference and belonging to the assignee of this disclosure. A piston-type pump may be used in the embodiments in place of a membrane-type pump. A bladder-type pump may also be used in the embodiments in place of a membrane-type pump, and a skilled person would understand that the pump mechanisms described may also be used with a bladder-type pump and vice versa.

A bladder-type pump has an interior fluid chamber surrounded by an airtight material. When the interior chamber is expanded, the opposing walls are moved away from each other by extending at least one side wall of the pump. The side walls of the bladder-type pump may have an accordion-like shape or be formed of a polymeric material which allows for the increase in distance between the opposing walls.

A membrane-type pump has at least one wall of flexible material and a second opposing wall which may be rigid or flexible. The edges of the two walls are attached to each other such that when a force applies to the pump to expand the interior fluid chamber, the force deforms at least the flexible wall, and the flexible wall arcs outward to form an interior fluid chamber. To allow for deformation, the flexible wall may be made of a polymeric material including elastomeric material such as rubber or plastic.

The bladder-type pump and membrane-type pump are arranged so that when no force applies to the pump or no weight is placed on the prosthetic system the volume of the interior fluid chamber is zero or near-zero. The pumps described and shown have a cylindrical shape. A skilled person would understand that the pumps may have a variety of shapes, for example, a diamond, rectangular, or triangular shape.

The specific embodiments of the prosthetic system will now be described regarding the figures.

FIGS. 1-2 show an embodiment of a prosthetic system 5 comprising a pump system 3 and a prosthetic foot 4. As seen in FIG. 1, the prosthetic foot 4 includes an ankle portion 6. The ankle portion 6 can include a first connection portion 8 such as a pyramid connector. The first connection portion 8 can attach to a stump on user, to another prosthetic system, or to any other appropriate object. It will be understood that the first connection 8 can include attachment features other than a pyramid connector, such as a threaded hole or screw, a latch, a magnetic member, tube clamp, or other features. The ankle portion 6 can additionally include second and third connection portions 10, 12. Optionally, the ankle portion 6 can include or define a cover. The cover can protect various components of the prosthetic foot 4 such as electronics or other components.

The ankle portion 6 can connect to an upper foot element 14 at the third connection point 12. The upper foot element 14 can be substantially plate-like and can have a generally rectangular cross-section along its length.

The third connection point 12 can provide a rotatable connection, although non-rotatable connections can also be used. In some embodiments, the rotation can be provided about an axle firmly mounted to the ankle portion 6, about which the upper foot element 14 can rotate. In other embodiments, the upper foot element 14 can be fixed to the axle, and relative rotation can be allowed between the axle and ankle portion 6. An attachment portion 15 can be disposed at the proximal end of the upper foot element 14. The attachment portion 15 can include or define a bushing or opening through which the axle extends. The attachment portion 15 can be integral to the proximal end of the upper foot element 14 or a separate structure.

The upper foot element 14 can be formed from a sufficiently flexible material such as carbon fiber. The upper foot element 14 can be substantially inelastic, so as to provide a rigid connection. It will be understood that the lower foot element and intermediate foot element (described below) can be formed of similar materials and have similar connections as the upper foot element 14.

The upper foot element 14 can be formed into a shape arranged to provide a desired flexibility or rigidity. As seen, the upper foot element 14 can include a concave-forward portion 18 at or near the attachment portion 15, although other shapes are also possible such as an L-shape or J-shape. The upper foot element 14 can extend from the lower portion of the concave-forward portion 18 into a foot portion 20. The foot portion 20 can further include a slit that extends longitudinally to separate the foot portion 20 into two or more foot members that can flex independently. In other embodiments, the foot portion 20 can be monolithic without any slits.

The ankle portion 6 can connect to a connection unit 22 at the second connection portion 10. Like the third connection portion 12, the second connection portion 10 can be rotatable or non-rotatable. In some embodiments, the third connection portion 12 is in front of the ankle portion 6, and the second connection portion 10 is in a rear portion of the ankle portion 6. The connection unit 22 is located at a rear portion of the prosthetic foot 4. However, in other embodiments, the connection unit 22 can be positioned in a front portion of the prosthetic foot.

The connection unit 22 can be in a variety of forms such as a connection member, an actuator, a rod connector, a rigid member, or a piston cylinder. The connection unit 22 can be operated in a variety of ways, as described by example, in U.S. Pat. No. 7,896,927 and U.S. patent application Ser. No. 12/816,968, each of which is incorporated herein by reference in its entirety.

The connection unit 22 is depicted as connecting to an intermediate foot element 24 at a fourth connection portion 26. The fourth connection portion 26 can be rotatable or non-rotatable. The intermediate foot element 24 can include or define a bushing or opening through which an axle extends to provide a rotatable connection or pivot axis between the intermediate foot element 24 and the connection unit 22. The intermediate foot element 24 can be substantially plate-like and can have a generally rectangular cross-section along its length.

The intermediate foot element 24 can extend into a foot portion in a manner similar to the foot portion 20 of the upper foot element 14. The intermediate foot element 24 can include a slit similar to the slit of the upper foot element 14. The intermediate foot element 24 is disposed below the upper foot element 14, and extends tangentially forward and toward the upper foot element 14 to abut the upper foot element 14 along the foot portion 20 of the upper foot element 14. Although the upper and intermediate foot elements 14, 24 are depicted as ending at approximately the same point, in some embodiments the upper foot element 14 may extend further, or the intermediate foot element 24 may extend further.

The prosthetic foot 4 can further include a lower foot element 28. The lower foot element 28 can extend from a heel portion 30 (e.g., a cantilevered or free end) at a bottom and rear portion of the prosthetic foot 4. This heel portion 30, as shown, can be spaced from the connection unit 22 and the intermediate foot element 24, curving downward toward and away from the connection unit 22. From the heel portion 30, the lower foot element 28 can extend to a toe portion 16 of the prosthetic foot 4, and can generally abut the foot portion of the intermediate foot element 24, as that member abuts the upper foot element 14. In the illustrated embodiment, the lower foot element 28 extends forward beyond the upper foot element 14 and the intermediate foot element 24. The lower foot element 28 can have a slit that generally matches the slits in the upper and intermediate foot elements.

The prosthetic foot 4 can include one or more fastening members that couple two or more of the elements 14, 24, 28 to each other. Alternatively, two or more of the elements 14, 24, 28 can be coupled together with an adhesive or other suitable mechanism.

Attachment can be provided between the elements 14, 24, 28, for example, generally in a metatarsal region of the prosthetic foot 4. Where the elements 14, 24, 28 are not held together (e.g., by the fastener members) they can separate and act as distinct flexible members instead of combining into a single flexible member where held together.

Optionally, the position of the one or more fastening members can be adjustable along the length of a slit defined in one or more of the elements 14, 24, 28. Thus, if the fastener member is moved forward, the elements 14, 24, 28 are held together over a shorter range, allowing more separation between them, and thus greater flexibility (e.g., the lever arm of the intermediate foot element 24 is relatively longer, resulting in greater flexibility of the prosthetic foot 4.) Alternatively, if the fastener member is moved rearward, the elements 14, 24, 28 are held together over a longer range, reducing the allowed separation and flexibility (e.g., the lever arm of the intermediate foot element 24 is relatively shorter, resulting in increased stiffness of the prosthetic foot 4). Advantageously, the one or more fastener members may be adjustable to vary the stiffness of the prosthetic foot 4.

In some embodiments, the flexibility and resistance of the elements 14, 24, 28 can be altered by the connection unit 22 (independently of, or in combination with, the one or more fastening members). Thus, it will be understood that the flexibility and resistance of the elements 14, 24, 28 can be altered manually and/or by an actuator.

In use, the prosthetic foot 4 can expand and compress. The prosthetic foot 4 is in expansion when the ankle portion 6 rotates in a counter-clockwise direction (e.g., the first connection portion 8 on the ankle portion 6 rotates away from the toe portion 16 of the prosthetic foot 4) and the connection unit 22 pushes the rear portion of the intermediate foot element 24 away from the upper foot element 14, increasing a distance 34 defined between the intermediate foot element 24 and the upper foot element 14. It will be appreciated that the prosthetic foot 4 can be in expansion independent of rotation of the ankle portion 6. For instance, the connection unit 22 can be an actuator that pushes the rear portion of the intermediate foot element 24 away from the upper foot element 14 to move the foot into expansion.

The prosthetic foot 4 is in compression when the ankle portion 6 rotates in a clockwise direction (e.g., the first connection portion 8 on the ankle portion 6 rotates toward the toe portion 16 of the prosthetic foot 4) and the connection unit 22 pulls the rear portion of the intermediate foot element 24 toward from the upper foot element 14, closing the distance 34. It will also be appreciated that the prosthetic foot 4 can be in compression independent of rotation of the ankle portion 6. For instance, the connection unit 22 can be an actuator that pulls the rear portion of the intermediate foot element 24 toward the upper foot element 14 to move the foot into compression. The prosthetic foot 4 may be insertable into a foot cover 21 as seen in FIG. 2.

An example of the prosthetic foot 4 is described in greater detail in U.S. patent application Ser. No. 14/188,216, filed on Feb. 24, 2014, and commercially available as the PRO-FLEX by Össur hf. This disclosure is incorporated by reference and belongs to the assignee of this disclosure.

In order to better understand the operation of the prosthetic foot 4, a basic discussion of the gait cycle is required. The gait cycle defines the movement of the leg between successive heel contacts of the same foot. The gait cycle has two phases: stance and swing. Of particular interest is the stance phase which generally includes heel-strike or initial contact, mid-stance, and toe-off.

It is during the stance phase that the mechanics of the prosthetic foot 4 come into play. Upon heel strike, the prosthetic foot 4 is in expansion, providing cushioning to the user. During mid-stance, at which time the weight of the user is transmitted through the prosthetic foot 4 to a support surface, the prosthetic foot 4 moves from expansion into compression. The prosthetic foot 4 remains in compression through toe-off until the weight of the user is removed from the prosthetic foot, at which time the prosthetic foot 4 returns to its resting position.

The pump system 3 includes a pump mechanism 2 and a securing member 36. The pump mechanism 2 can be coupled to the prosthetic foot 4 at any suitable location, but is shown coupled to the concave-forward portion 18 located at or toward the proximal end of the upper foot element 14. The pump mechanism 2 can be made generally from carbon fiber and an elastomeric compound (e.g., a membrane) providing durable yet lightweight components. Prior art pump mechanisms are typically of heavy metal construction, which imposes a significant weight burden on the user when ambulating.

The pump mechanism 2 is operably connected to the intermediate foot element 24 and the securing member 36 secured to the attachment portion of the upper foot element 14. As described in more detail below, relative movement between the securing member 36 and the intermediate foot element 24 moves the pump mechanism 2 between an original configuration and an expanded configuration.

Figure 2A:
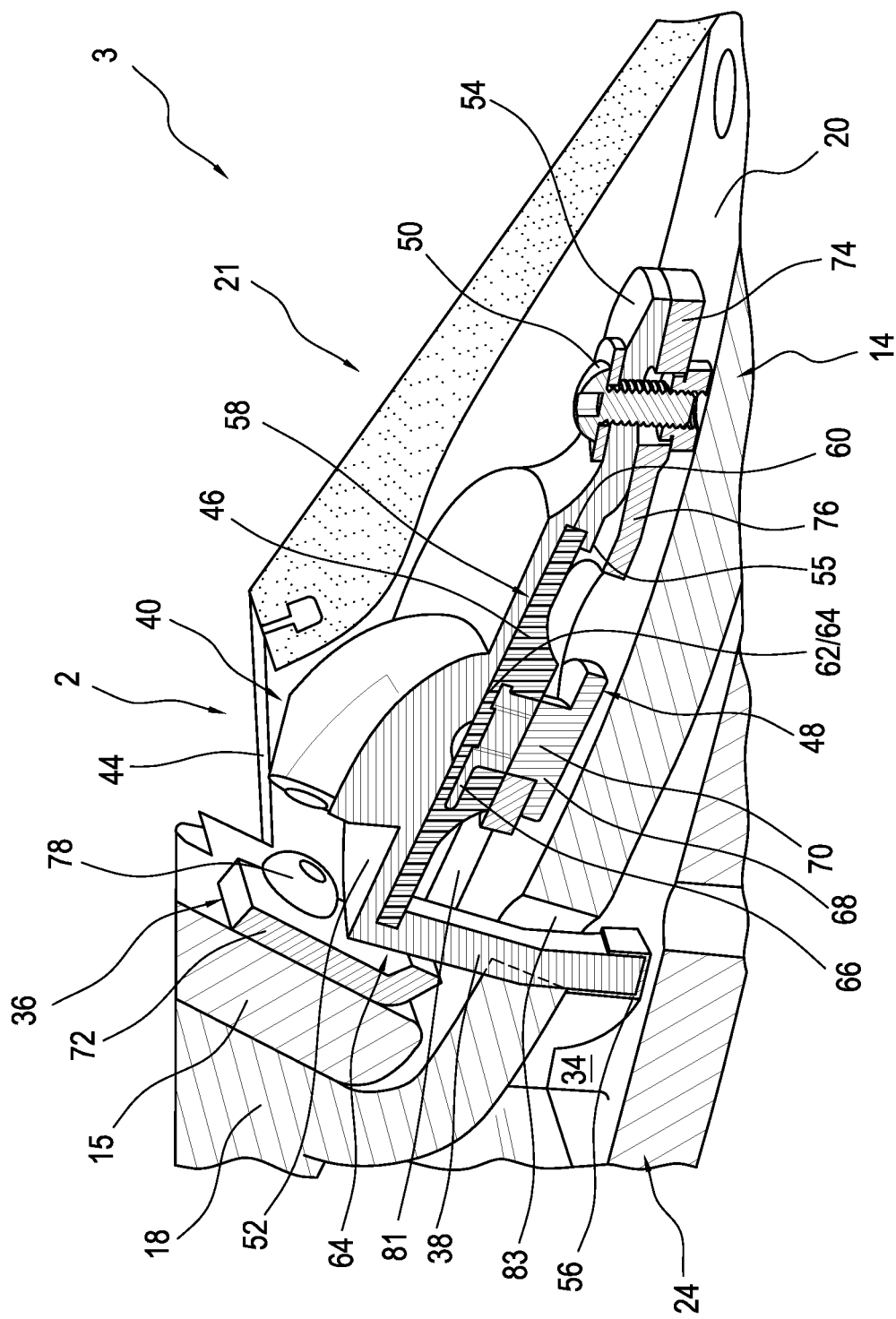
FIG. 2A shows a sectional view of the prosthetic system in FIG. 1 in a first configuration.

As best seen in FIG. 2A, the pump mechanism 2 includes a housing 40 containing two valve assemblies 42 (shown in FIG. 1), 44, a membrane 46, and a connector 48. The valve assemblies can include a one-way valve, also referred to as a check valve. A preferred type of one-way valve used is a duckbill valve. It should be appreciated however that other types of one-way valves are possible.

The valve assembly 42 is arranged to only allow fluid to enter the pump mechanism 2. The valve assembly 42 can be in fluid communication with the cavity of a prosthetic socket. When the volume of the pump mechanism 2 increases, fluid (e.g., air) can be drawn out from the socket via the valve assembly 42. The valve assembly 44 is arranged to only allow fluid to be expelled out of the pump mechanism 2, preferably to atmosphere.

The housing 40 can be coupled to the securing member 36 via at least one fastener 50 situated at a front portion of the housing 40 and securing member 36. It should be appreciated that the pump mechanism 2 and/or pump system can be a separate add-on module to the prosthetic foot 4. For example, the pump mechanism 2 can be removably attached to the securing member 36 via the fastener 50 and the connector 48. Because the pump mechanism 2 is not integrated into the prosthetic foot 4, failure of the pump mechanism 2 advantageously would not affect the performance of the prosthetic foot 4.

The housing 40 can have a rigid configuration. The housing 40 can define a main portion 52, a front portion 54, and a rear portion 64 opposite the front portion 54. The main portion 52 can have any shape but is shown having a generally cylindrical shape. The front portion 54 can have an elongate configuration and extend forwardly over an upper surface of the securing member 36.

The housing 40 can have a width that tapers from the main portion 52 to the front portion 54 such that the front portion 54 is narrower than the main portion 52. This advantageously can facilitate the pivoting and/or flexing of the housing 40 in the area of the front portion 54. According to a variation, the bottom surface of the front portion 54 can include a rocker-like curvature 55 that allows the housing 40 to rock back and forth as the pump mechanism 2 moves between original and expanded configurations described below.

The front portion 54 can define a hole arranged to receive a shaft of the fastener 50. The rear portion 64 of the housing 40 defines an arm member 38 arranged to move or drive the pump mechanism 2 toward at least an expanded configuration (described below) upon movement of the intermediate foot element 24 relative to the upper foot element 14. The arm member 38 extends generally downward from the main portion 52 and has a lower end including an engagement surface 56 arranged to selectively engage with the upper surface of the intermediate foot element 24. The arm member 38 has a rigid configuration. The arm member 38 is shown as a push member but can comprise any suitable member.

The bottom surface of the main portion 52 of the housing 40 defines a cavity 58 that is provided with an undercut circumferential groove 60 between an open end of the cavity 58 and a closed bottom 62 of the cavity 58. An outer radial edge portion of the membrane 46 can be situated in the circumferential groove 60 such that a seal is formed between the membrane 46 and the housing 40. Optionally, an adhesive can be applied between the housing 40 and the outer radial edge portion of the membrane 46, increasing the sealing effect. The bottom 58 of the cavity 50 can define two openings which extend into the housing 40 to form internal passageways providing fluid communication between a fluid chamber defined below and the one-way valve assemblies 42, 44.

Figure 2B:
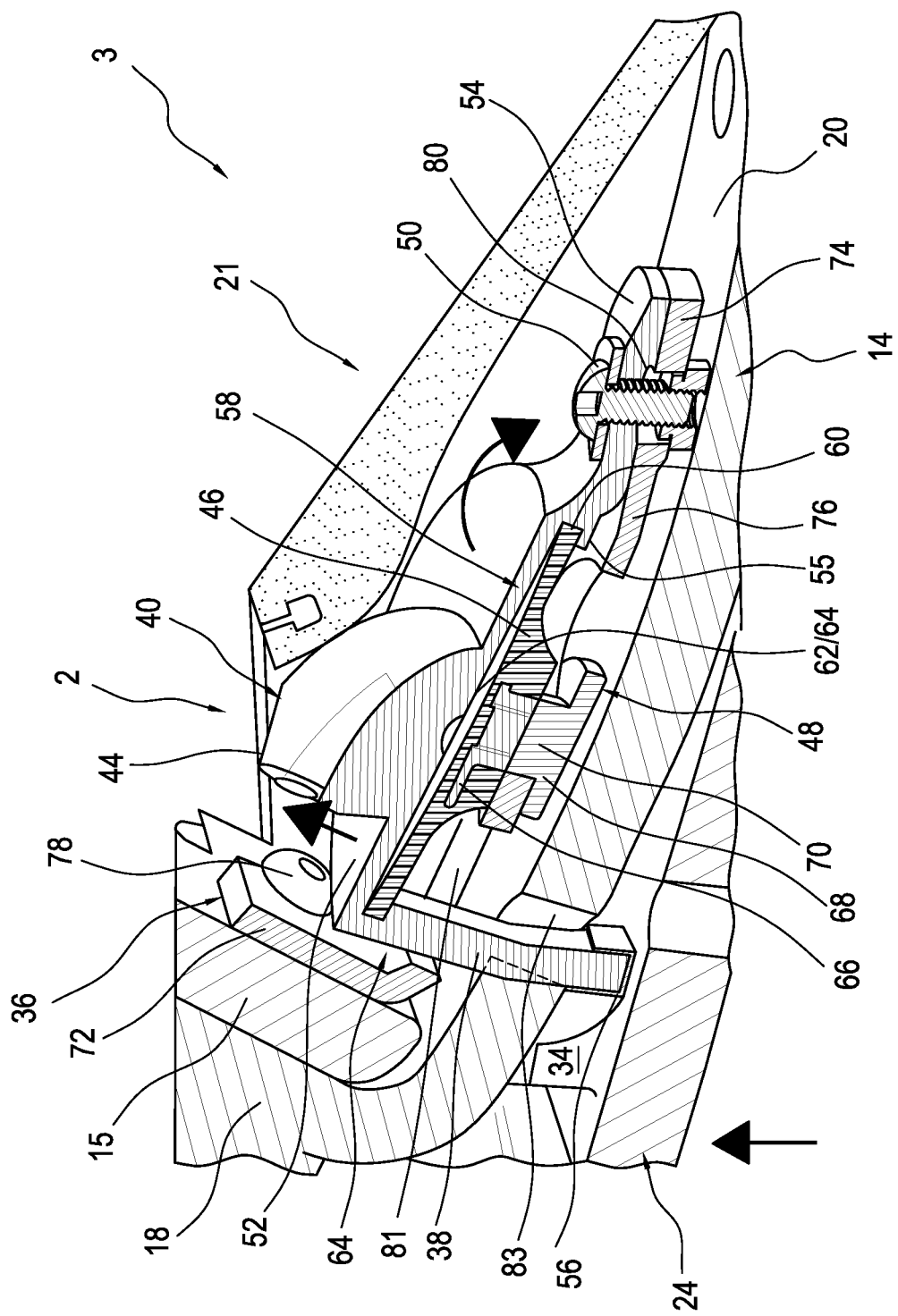
FIG. 2B shows a sectional view of the prosthetic system in FIG. 1 in a second configuration.

The pump mechanism 2 is movable between an original configuration in which the volume of a fluid chamber 64 defined between the top surface of the membrane 46 and the bottom 62 of the cavity is zero or near-zero (shown in FIG. 2A), and an expanded configuration in which the volume of the fluid chamber 64 is increased (shown in FIG. 2B).

The bottom 62 of the cavity 58 can substantially complement the top surface of the membrane 46 such that when no force is exerted on the pump mechanism 2 it is in the original configuration. Both the bottom 62 of the cavity 58 and the top surface of the membrane 46 can be generally flat.

When a force is exerted on the membrane 46 in a direction away from the housing 40, the pump mechanism 2 moves toward the expanded configuration (shown in FIG. 2B) as the force pulls a portion of the membrane 46 away from the bottom 62 of the cavity 58, causing deformation of the membrane 46 and an increase in volume of the fluid chamber 64. This increase in volume of the fluid chamber 64 can draw fluid into the fluid chamber 64 from the socket through the one-way valve assembly 42. The housing 40 may be formed of metal such as stainless steel, carbon fiber, or plastic or any other material which would provide sufficient strength to resist deformation when pulled away from the membrane 46.

Once the force is removed from the membrane 46, the pump mechanism 2 returns toward its original configuration as the membrane 46 returns toward the bottom 62 of the cavity 58 and fluid within the fluid chamber 64 is expelled out of the one-way valve assembly 44. The membrane 46 can be elastomeric and can use at least in part its material properties to naturally or elastically return to its original position on the bottom 62 of the cavity 58.

The membrane 46 may have any desired shape, but is shown having a generally circular or elliptical shape. The membrane 46 can be operatively attached at or near its center point to the securing member 36 while the outer radial edge portion of the membrane 46 is attached to the housing 40 such that when the membrane 46 is pulled away from the housing 40 a pocket forms in a middle area of the membrane 46 due to the deformation of the membrane 46. The formation of the pocket increases the volume of the fluid chamber 64. The pump mechanism 2 thus uses a compliant membrane to create suction.

The connector 48 can have an upper radial flange 66 embedded in the membrane 46, a lower radial flange 68 below the membrane 46, and a shaft portion 70 extending between the upper flange 66 and the lower flange 68. Optionally, the connector 48 may be of a two-piece construction such that the lower flange 68 can be threadedly removed from the upper flange 66 in the membrane 46. The connector 48 may be formed of metal, plastic, or any other suitable material. The upper flange 66 may extend substantially into the membrane 46 or may be formed of a material that is part of the membrane 46 (e.g., a flexible metal member).

The securing member 36 can be a plate defining a rear portion 72, a front portion 74, and a middle portion 76 extending between the rear portion 72 and the front portion 74. The rear portion 72 defines a part extending generally upward that is attached to the attachment portion 15 of the upper foot element 14. The securing member 36 can be connected to the upper foot element 14 in any suitable manner but is shown attached via a fastener 78. The rear portion 72 can define an aperture for receiving the fastener 78 to connect the securing member 36 to the upper foot element 14.

The middle portion 76 and front portion 74 extend forwardly from the rear portion 72 above the foot portion 20 of the upper foot element 14. The securing member 36 can have a flexible, rigid, and/or semi-rigid configuration.

The securing member 36 can be operatively connected to the membrane 46 via the connector 48. The middle portion 76 of the securing member 36 can define a connector opening 80. The connector opening 80 can have a diameter that is oversized relative to the lower flange 68 of the connector 48.

To attach the pump mechanism 2 and connector 48 to the securing member 36, the shaft portion 70 and lower flange 68 of the connector 48 can be inserted through the connector opening 80. The connector 46 with the pump mechanism 2 can then be slid toward the rear portion 72 until the upper surface of the lower flange 68 engages a lower surface of the securing member 36 along the rearward side of the opening 80, properly positioning the pump mechanism 2 on the securing member and a portion of the lower flange 68 below the securing member 36. In this position, the housing 40 can be coupled to the securing member via the fastener 50, securing the membrane 46 to the securing member 36 via the connector 46. Through the structure of the connector 46 and the securing member 36, the securing member 36 and/or the pump mechanism 2 has the benefit of being easily and quickly removed and/or replaced from the prosthetic foot 4.

The securing member 36 defines a first through hole 81 and the upper foot element 14 defines a second through hole 83 through which the arm member 38 extends from the main portion 52 of the housing 40 toward the upper surface of the intermediate foot element 24. As such, portions of the arm member 38 are entirely surrounded by the upper foot element 14 or the securing member 36. This advantageously helps the prosthetic system maintain a low-profile configuration by routing the arm member 38 through the prosthetic foot 4 rather than around the prosthetic foot 4. It also beneficially helps protect the arm member 38 from inadvertent contact with external objects.

The securing member 36 can be formed of carbon fiber or another suitable material. The location, shape, and/or length of the opening 80 and/or first and second through holes 81, 83 can be adjusted based on the size of the prosthetic foot 4 and/or pump mechanism 2, the weight of the user, and/or other factors.

FIGS. 1 and 2A show the prosthetic foot in its resting position. When the prosthetic foot 4 is in the resting position, the engagement surface 56 on the arm member 58 can be lightly resting on or a small distance above the upper surface of the intermediate foot element 24, and the pump mechanism 2 is in its original configuration.

Upon heel strike, the prosthetic foot 4 moves into expansion, which, in turn, causes the connection unit 22 to push the intermediate foot element 24 away from the engagement surface 56 of the arm member 38. With the prosthetic foot 4 in expansion, the pump mechanism remains in its original configuration.

As the prosthetic foot 4 moves from heel strike through mid-stance and/or toe-off, the prosthetic foot 4 moves into compression. In compression, the connection unit 22 pulls the intermediate foot element 24 toward the upper foot element 14, closing the distance 34 and applying an upward force on the engagement surface 56 of the arm member 38 as shown in FIG. 2B.

Referring still to FIG. 2B, the arm member 38 transfers the upward force on the engagement surface 56 to the housing 40, forcing the back portion 64 of the housing 40 away from the securing member 36. This causes the housing 40 to pivot and/or flex around the front portion of the housing 40 attached to the securing member 36, which, in turn, pulls the membrane 46 away from the housing 40, driving the pump mechanism 2 toward the expanded configuration. More particularly, the arm member 38 drives the housing 40 away from the membrane 46 to deform the membrane 46 between the securing member 36 and the housing 40, increasing the volume of the fluid chamber 64.

This increase in volume of the fluid chamber 64 creates a vacuum in the pump mechanism 2, pulling fluid into the pump mechanism 2 through the one-way valve assembly 42. Compression of the prosthetic foot 4 thus automatically creates a vacuum in the pump mechanism 2. This is advantageous over prior art prosthetic devices that require compression of the pump to expel air before the pump can be decompressed to draw in air. Further, because the pump mechanism 2 does not need to be first compressed before it can create a vacuum upon decompression, the pump mechanism 2 can achieve smaller fluctuations in air pressure than the prior art devices, so the difference between the greatest pressure and lowest pressure in the vacuum space of the socket is less than compared to the prior art devices.

At the end of the stance phase or when the weight of the user is removed from the prosthetic foot 4, the prosthetic foot 4 returns to its resting position and the inherent properties of the housing 40 and/or membrane 46 can help move the pump mechanism 2 back toward its original configuration and decrease the volume of the fluid chamber 64 to a zero or near zero volume.

During the return of the membrane 46 toward the housing 40, the pump mechanism 2 expels fluid in the fluid chamber 64 out of the one-way valve assembly 44. Because the pump mechanism 2 returns to its original configuration of zero or near-zero volume in the fluid chamber 64 at the beginning or end of each gait cycle, all fluid drawn into the pump mechanism 2 is automatically expelled. This is advantageous because prior art devices rely on complete compression of the pump in expelling air in each gait cycle to use the pump to its maximum capacity. It is difficult for complete compression to occur in every cycle using the gait of a user as the actuating force since the impact and displacement of the pump is not consistent and varies between users.

To meet the stiffness/flexibility, strength, and weight requirements needed for use on the prosthetic foot, the securing member 36 and/or arm member 38 can be made of a durable but flexible material such as carbon fiber cloth, unidirectional composites, plastic, or metal.

Figure 3:
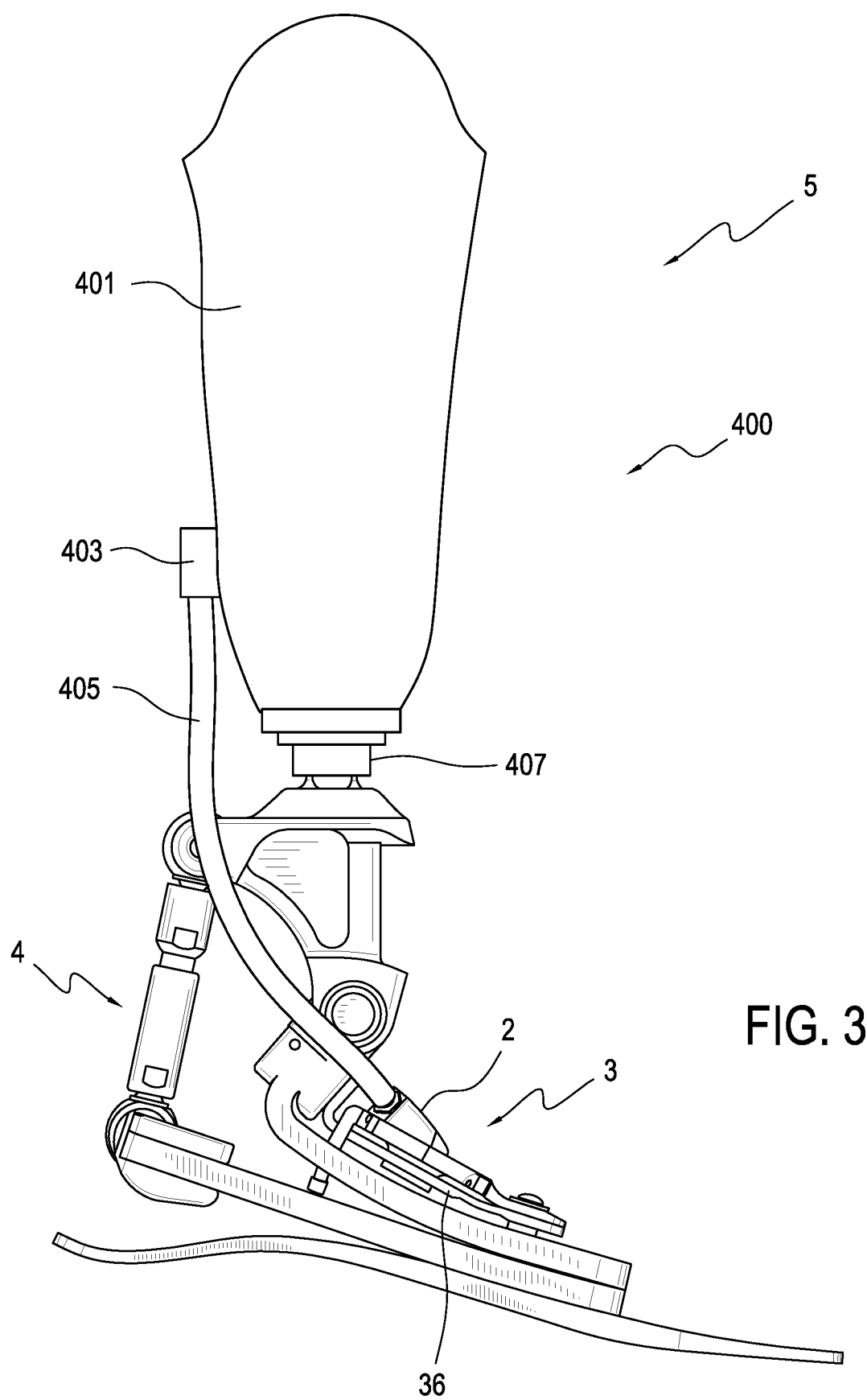
FIG. 3 shows a prosthetic system with a pump system according to another embodiment.

FIG. 3 includes a prosthetic system 5 comprising a vacuum suspension system 400 including the pump system 3 and the prosthetic foot 4. The vacuum suspension system 400 has a socket 401, a liner preferably including a seal component, a valve assembly 403, a tube 405 connecting the pump mechanism 2 to the socket 401, and the prosthetic foot 4. The socket 401 defines an interior space, and an interior wall delimiting the interior space. The vacuum suspension system 400 may also employ an adaptor system 407. Alternatively, the adaptor system 407 can be replaced with a shock and/or rotation module.

The vacuum suspension system 400 provides improved proprioception and volume control since there is better attachment between the socket 401 and the residual limb. The vacuum suspension system 400 includes the pump system 3 having the pump mechanism 2 and the securing member 36, as described above, which provide a vacuum assisted suspension by generating a negative pressure (vacuum) inside the socket 401.

The function of the vacuum suspension system 400 can be fully automatic. During mid-stance and/or toe-off, compression of the prosthetic foot 4 expands the pump mechanism 2 to efficiently draw fluid out of the socket 401 in each step. During the swing phase, decompression of the prosthetic foot 4 permits the pump mechanism 2 to return to its original position, expelling the fluid drawn from the socket 401 to atmosphere. The pump mechanism 2 thus can create a negative pressure inside the socket 401, resulting in a secure and reliable elevated vacuum suspension that provides an intimate suspension as the negative pressure formed inside of the socket 401 holds the liner and the residual limb firmly to the socket wall.

Figure 4:
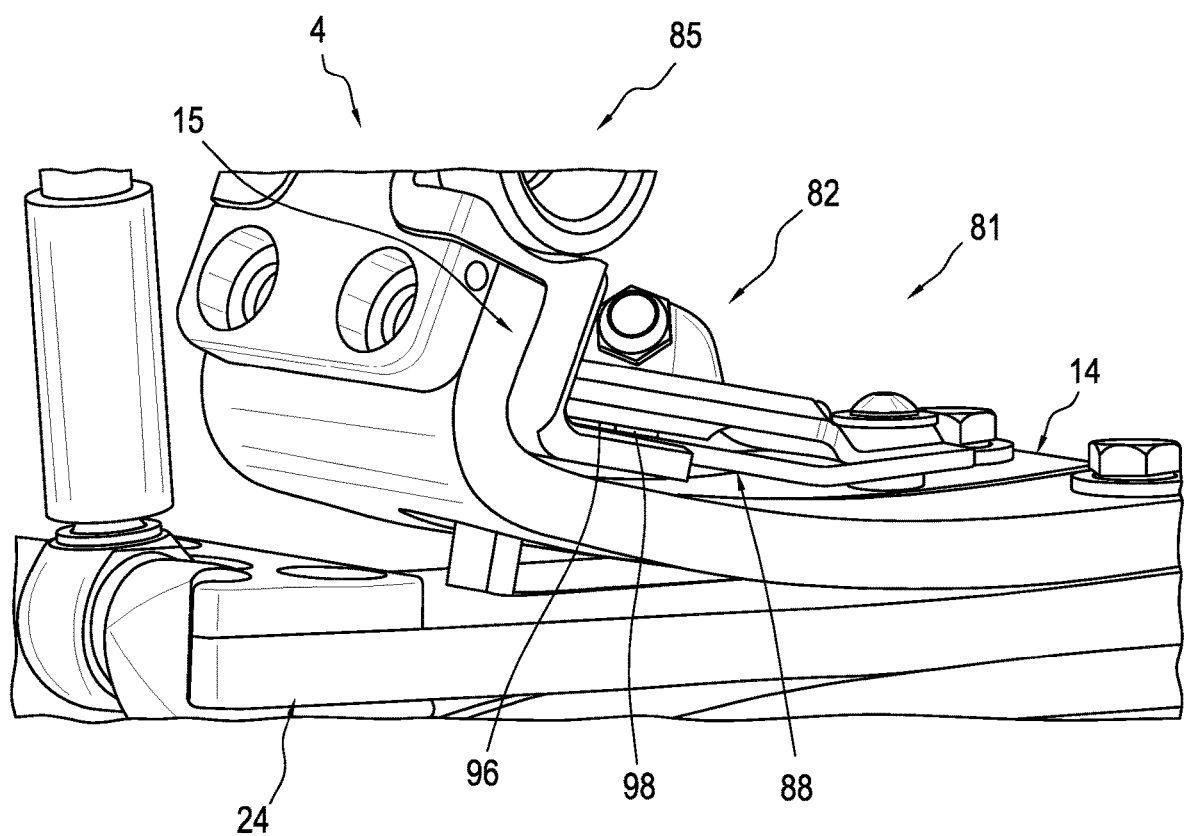
FIG. 4 shows a prosthetic system with a pump system according to another embodiment.
Figure 5:
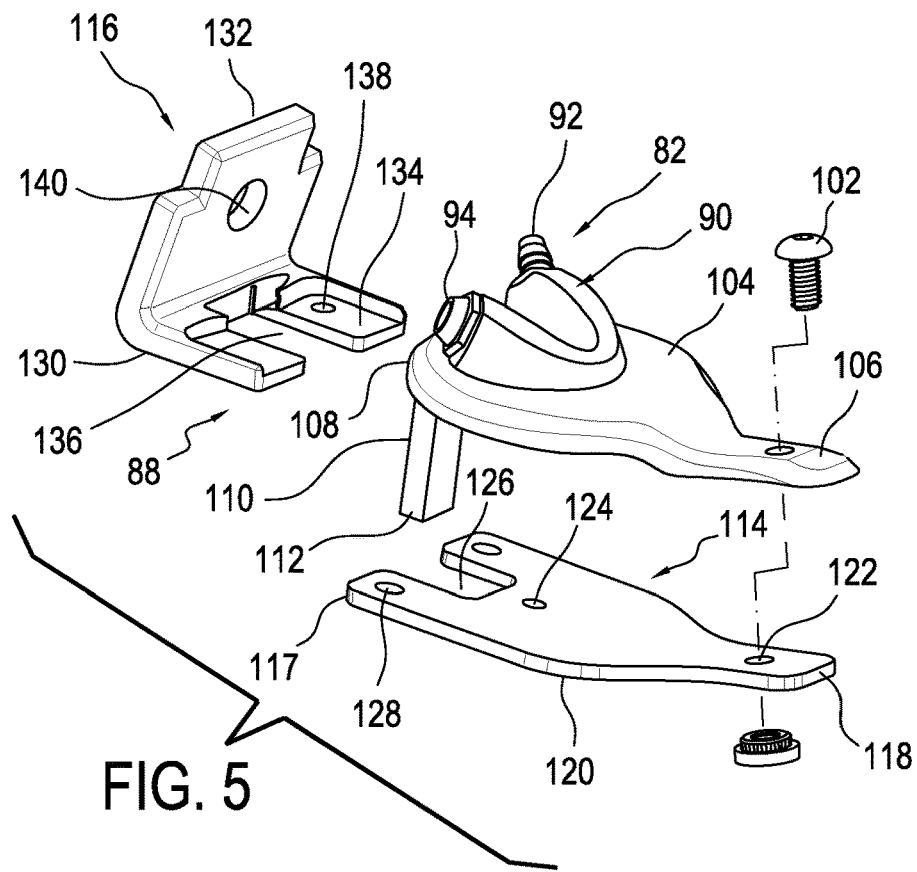
FIG. 5 shows an exploded view of the pump system in FIG. 4.
Figure 6:
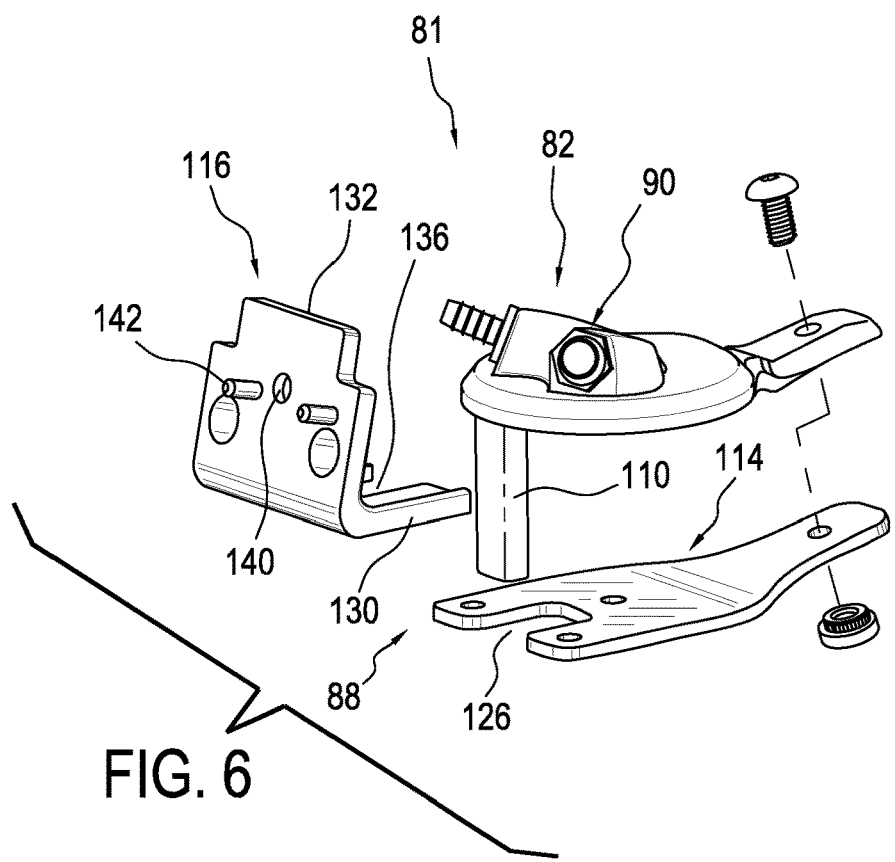
FIG. 6 shows another exploded view of the pump system in FIG. 4.

Another embodiment of a prosthetic system 85 is shown in FIGS. 4-6. This embodiment can be similar to the first embodiment illustrated in FIGS. 1-3. As seen in FIG. 4, the prosthetic system includes the prosthetic foot 4 and a pump system 81. The pump system 81 includes a pump mechanism 82 and a securing member 88. The pump mechanism 82 is attached to the securing member 88 and situated above the upper foot element 14 of the prosthetic foot 4. The pump mechanism 82 is operably connected to the intermediate foot element 24 via an arm member and the securing member 88 is secured to the attachment portion on the upper foot element 14.

Referring to FIGS. 5 and 6, the pump mechanism 82 includes a housing 90 containing two one-way valve assemblies 92, 94, a membrane 96 (shown in FIG. 4), and a connector 98 (shown in FIG. 4). The valve assembly 92 only allows fluid to enter the pump mechanism 82 which can be in fluid communication with the cavity of a socket. The valve assembly 94 only allows fluid to be expelled out of the pump mechanism 82, preferably to atmosphere. The connector 98 can include an upper radial flange embedded in the membrane 96, a lower radial flange below the membrane 96, and a shaft portion extending between the upper and lower flanges.

The housing 90 can be coupled to the securing member 88 via at least one fastener 102 situated at a front portion of the housing 90 and the securing member 88. The housing 90 can have a rigid configuration. The housing 90 defines a main portion 104, a front portion 106, and a rear portion 108 opposite the front portion 106. The front portion 106 can have an elongate configuration and extend forwardly over an upper surface of the securing member 88. The rear portion 108 of the housing 90 can define an arm member 110 extending generally downward from the housing 90 and arranged to move or drive the pump mechanism 82 toward at least an expanded configuration (described below) upon movement of the intermediate foot element 24 relative to the upper foot element 14. The arm member 110 can comprise a push member having a lower end defining an engagement surface 112 arranged to engage with the upper surface of the intermediate foot element 24. The arm member 110 can have a rigid configuration.

Similar to the pump mechanism 2, the pump mechanism 82 relies upon deformation of the membrane 96 to move between an original configuration in which the volume of a fluid chamber defined between the top surface of the membrane 96 and the bottom of the housing 90 is zero or near-zero, and an expanded configuration in which the volume of the fluid chamber is increased. The housing 90 is arranged to surround the outer radial edge portion of the membrane 96 and creates a seal with the membrane 96. The bottom surface of the housing 90 can define a pair of openings which extend into the housing 90 to form internal passageways to provide fluid communication between the fluid chamber and the two one-way valve assemblies 92, 94.

The securing member 88 can comprise a plate member 114 and a backing portion 116. Optionally, the backing portion 116 and the plate member 114 can be made of different materials. For instance, the plate member 114 can be made of carbon fiber cloth and the backing portion 116 can be made of metal, plastic, or another suitable material, facilitating production. Moreover, because the securing member 88 includes a two part construction, the length, curvature, and/or shape of the plate member 114 can be advantageously adjustable or customizable without having to replace the entire securing member 88.

The plate member 114 can include a rear portion 117, a front portion 118, and a middle portion 120 extending between the rear and front portions 117, 118. The plate member 114 can be formed of carbon fiber cloth or another suitable material. The plate member 114 can have a width that tapers from the middle portion 120 toward the front portion 118 such that the front portion 118 is narrower than the middle portion 120.

The front portion 118 can define an aperture 122 for receiving the fastener 102 to connect the plate member 114 to the front portion of the housing 90. The middle portion 120 defines an aperture 124 for connecting the plate member 114 to the connector 98. A slot or notch 126 is formed in the terminal edge of the rear portion 117 that allows the arm member 110 to extend through the plate member 114. The rear portion 117 can define a pair of apertures 128 on opposing sides of the notch 126.

The backing portion 116 includes a base 130 and a back member 132. The upper surface of the base 130 defines a seat 134 arranged to accommodate the rear portion 117 of the plate member 114 when the plate member 114 is attached to the backing portion 116. This beneficially limits or prevents the plate member 114 from sliding sideways off of the backing portion 116. A slot or notch 136 is defined in the base 130 that generally corresponds to the notch 126 in the plate member 114, allowing the arm member 110 to extend through the base 130. The base 130 further defines a pair of apertures 138 in the seat 134 corresponding to the apertures 128 on the plate member 114 for receiving one or more fasteners to attach the plate member 114 to the backing portion 116.

The back member 132 can extend generally upward from a rear end of the base 130. The back member 132 can be generally perpendicular to the base 130 or oblique relative to the base 130. The back member 132 can define an aperture 140 for receiving a fastener to connect the backing portion 116 to the upper foot element 14 and/or the attachment portion 15 (shown in FIG. 4) of the foot 4.

The rear surface of the back member 132 can generally complement the front surface of the attachment portion 15. According to a variation, the rear surface of the back member 132 can define one or more alignment features including a pair of pin members 142 arranged to be received within a pair of corresponding openings defined in the attachment portion. These advantageously help align the fastener aperture 140 on the back member 132 and a fastener aperture on the attachment portion 15, facilitating connection and/or removal of the securing member from the foot.

Figure 7:
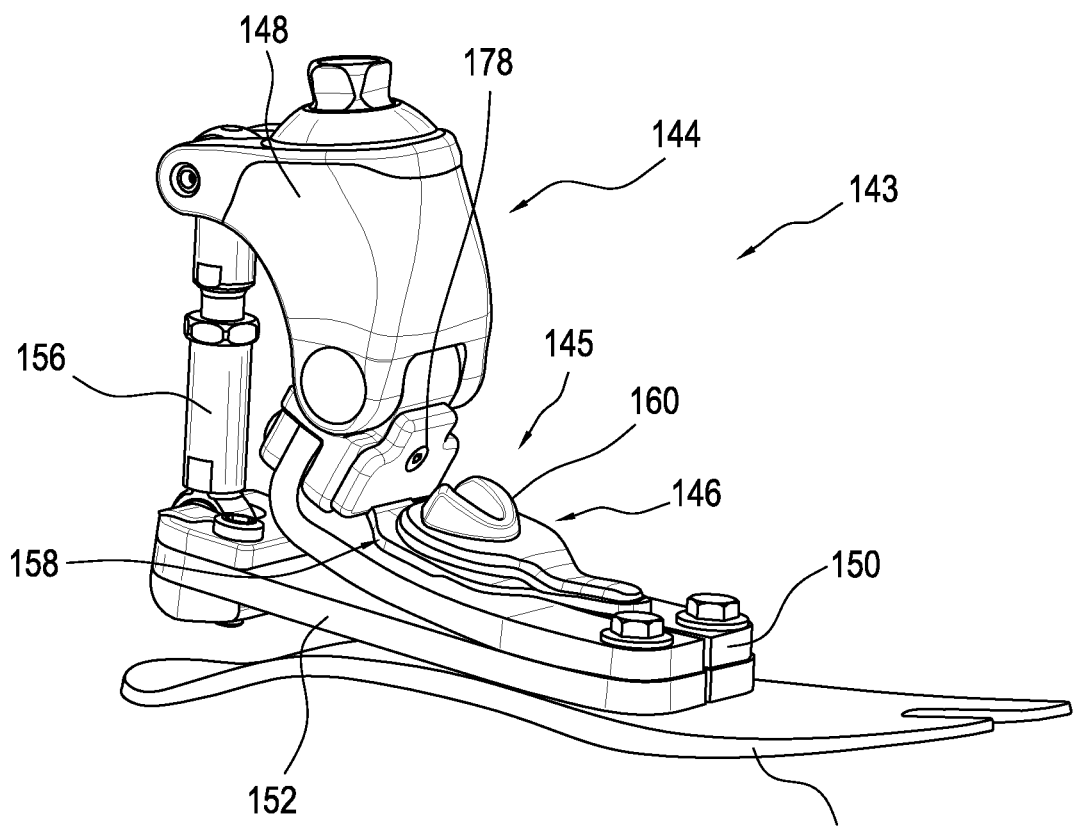
FIG. 7 shows a prosthetic system with a pump system according to another embodiment.
Figure 8:
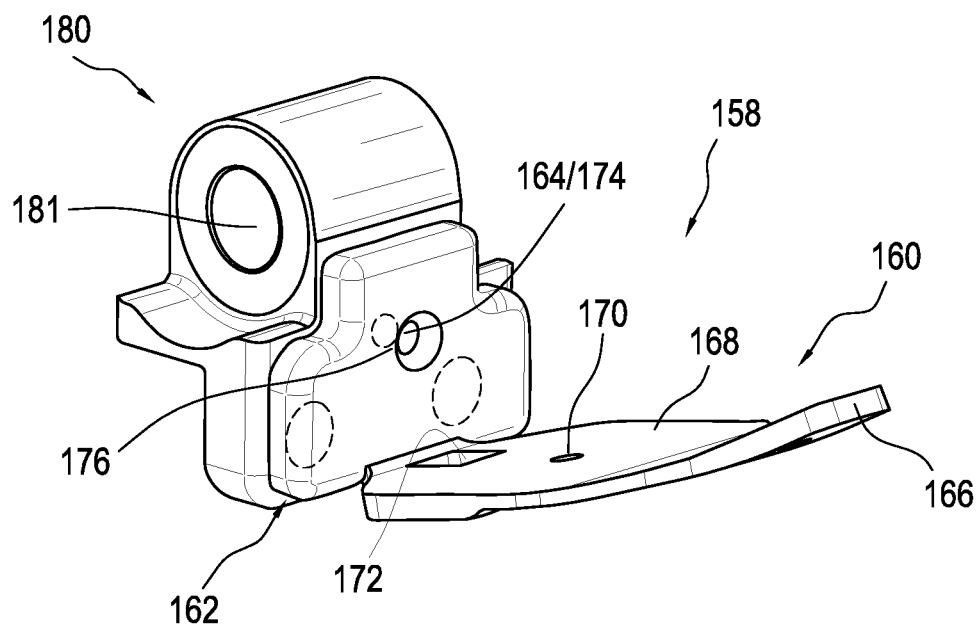
FIG. 8 shows the pump system in FIG. 1 removed from the prosthetic foot.

Another embodiment of a prosthetic system 143 is shown in FIGS. 7 and 8. This embodiment can be similar to the previously described embodiments. The prosthetic system 143 includes a prosthetic foot 144 and a pump system 145. The prosthetic foot 144 can be similar to other embodiments of the prosthetic foot. For instance, it can include an ankle portion 148 and an upper foot element 150 coupled to the ankle portion 148 via an attachment portion 180 (shown in FIG. 8). The attachment portion 180 can include or define a bushing or opening 181 through which an axle extends.

An intermediate foot element 152 is disposed generally below the upper foot element 150 and attached to the upper foot element 150 at a front portion thereof. The prosthetic foot 144 can have a lower foot element 154 disposed below the intermediate foot element 152. The lower foot element 154 extends rearwardly to a free end and extends forwardly to a toe portion of the foot 144. A connection unit 156 can extend between the rear of the ankle portion 148 and the rear portion of the intermediate foot element 152. In use, the prosthetic foot 144 can expand and compress.

The pump system 145 includes a pump mechanism 146 and a securing member 158. The pump mechanism 146 is situated above the upper foot element 150 and operably connected to the intermediate foot element 152 and the securing member 158 secured to the attachment portion 180 on the upper foot element 150.

The pump mechanism 146 can be configured similarly to the previously described pump mechanisms. For instance, the pump mechanism 146 can include a housing 160 containing two one-way valve assemblies, a membrane, and a connector. One of the valve assemblies only allows fluid to enter the pump mechanism 146 which can be in fluid communication with the cavity of a socket. The other valve assembly only allows fluid to be expelled out of the pump mechanism 146, preferably to atmosphere. The connector can be attached to the membrane and the securing member 158 and can exhibit any suitable configuration. For instance, the connector may be a single fastener or screw, allowing the pump mechanism 146 to easily retrofit on a prosthetic foot.

The pump mechanism 146 relies upon deformation of the membrane to move between an original configuration in which the volume of a fluid chamber defined between an upper surface of the membrane and the bottom of the housing 160 is zero or near-zero, and an expanded configuration in which the volume of the fluid chamber is increased. The housing 160 is arranged to surround the outer radial edge portion of the membrane and creates a seal with the membrane. The bottom of the housing 160 can define a pair of openings which extend into the housing 160 to form internal passageways to provide fluid communication between the fluid chamber and the two one-way valve assemblies.

As best seen in FIG. 8, the securing member 158 can exhibit a two-part construction. The securing member 158 can include a plate member 160 and a backing portion 162. Optionally, the backing portion 162 and the plate member 160 can be made of different materials.

The plate member 160 can include a rear portion 164, a front portion 166, and a middle portion 168 extending between the rear and front portions. The plate member 160 can be formed of carbon fiber cloth or another suitable material. The plate member 160 can have any suitable shape but is shown having a width that tapers from the middle portion 168 toward the front portion 166 such that the front portion 166 is narrower than the middle portion 168.

The middle portion 168 can define an aperture 170 for connecting the securing member 158 to the connector. A cutout 172 is defined in the plate member 160 at or near the rear portion 164 that allows an arm member of the pump mechanism 146 to extend through the plate member 160 toward the intermediate foot element 152. The rear portion 164 can define a connection tab 174 that extends generally upward from the plate member 160. The connection tab 174 can define an aperture for receiving a fastener 178 to connect the securing member 158 to the prosthetic foot 144.

The backing portion 162 extends generally upright or obliquely relative to the plate member 160. The backing portion 162 can define an internal cavity with an open bottom into which the connection tab 174 can be inserted. The backing portion 162 can also define an aperture 176 for receiving the fastener 178. As such, the connection tab 174 of the plate member 160 can be inserted into the backing portion 162. The connection tab 174 and the backing portion 162 can then be secured to the attachment portion 180 of the prosthetic foot 144 by inserting the fastener 178 through the apertures. This advantageously allows the securing member 158 to be directly attached to the prosthetic foot 144 using a single fastener as opposed to multiple fasteners, facilitating the retrofit of a prosthetic foot with the pump system.

Figure 9:
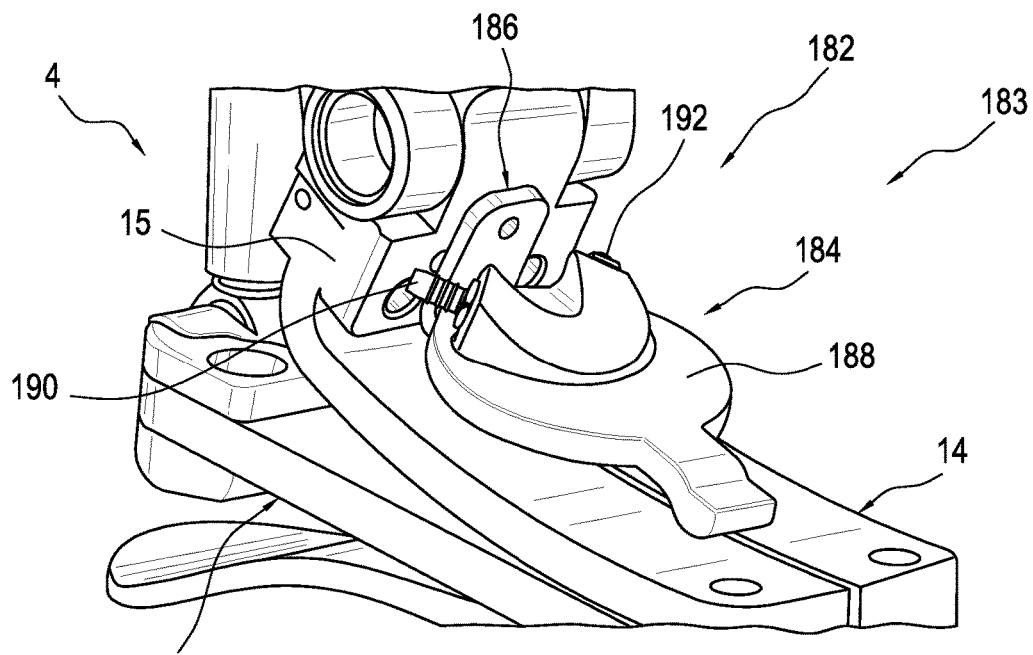
FIG. 9 shows a prosthetic system with a pump system according to another embodiment.
Figure 10:
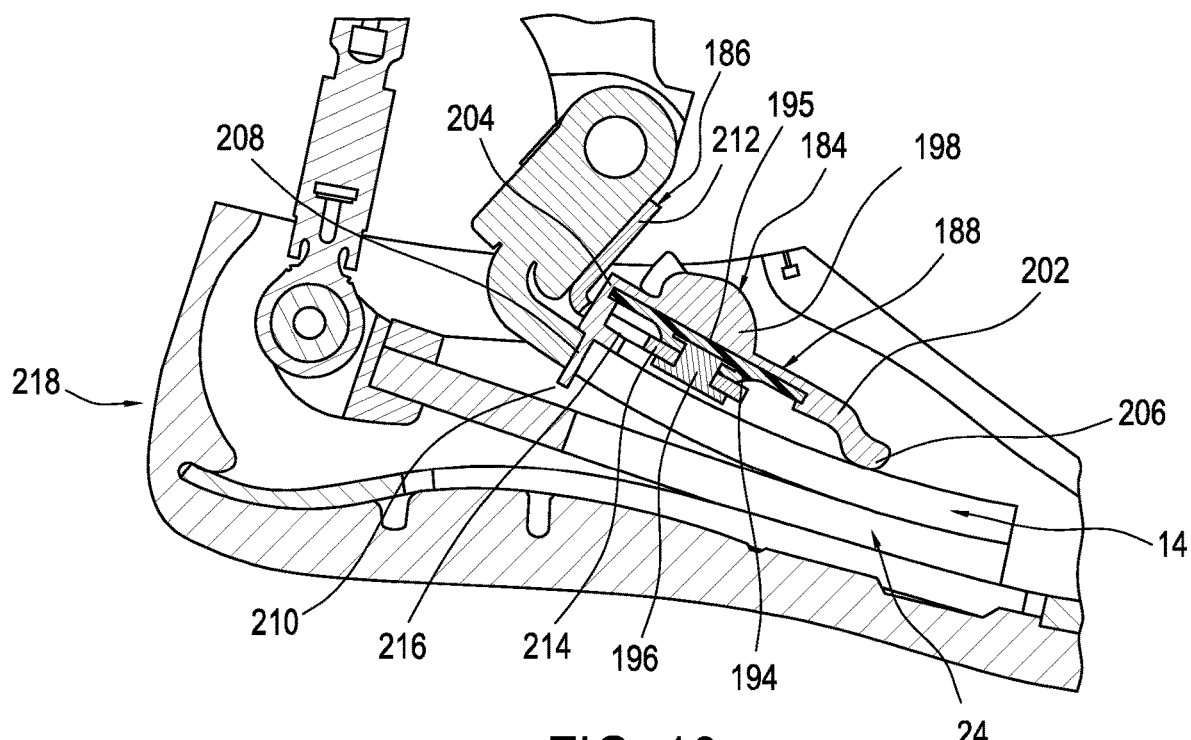
FIG. 10 shows a sectional view of the prosthetic system in FIG. 9.

Another embodiment of a prosthetic system 183 is shown in FIGS. 9 and 10. The prosthetic system comprises a pump system 182 and the prosthetic foot 4. The pump system 182 includes a pump mechanism 184 and a securing member 186. The pump mechanism 184 is attached to the securing member 186 and situated above the upper foot element 14. The pump mechanism 184 is operably connected to the intermediate foot element 24 via an arm member 208 and the securing member 186 is secured to the attachment portion 15 on the upper foot element 14. The prosthetic foot 4 may be insertable into a foot cover 218 as seen in FIG. 10.

The pump mechanism 184 includes a housing 188 containing two one-way valves 190, 192, a membrane 194, and a connector 196. The valve assembly 190 only allows fluid to enter the pump mechanism 184 and the valve assembly 192 only allows fluid to be expelled out of the pump mechanism 184. The connector 196 can include an upper radial flange embedded in the membrane 194, and a lower radial flange below the membrane 194, and a shaft portion extending between the upper and lower flanges.

The housing 188 can have a rigid configuration and can define a main portion 198, a front portion 202, and a rear portion 204 opposite the front portion 202. The front portion 202 can have an elongate configuration and extend forwardly and downwardly from the main portion 198 to a front edge 206 arranged to engage the upper surface of the upper foot element 14.

The rear portion 204 can define the arm member 208. The arm member 208 is arranged to drive or move the pump mechanism 184 toward at least an expanded configuration (described below) upon engagement with the intermediate foot element 24 and movement of the intermediate foot element 24 relative to the upper foot element 14. The arm member 208 can be any suitable mechanism but is shown comprising a push member extending generally downward to a lower end defining an engagement surface 210 arranged to engage with the upper surface of the intermediate foot element 24. The arm member 208 can have a rigid configuration.

Similar to the other pump mechanisms, the pump mechanism 184 relies upon deformation of the membrane 194 to move between an original configuration in which the volume of a fluid chamber 195 defined between the top surface of the membrane 194 and the bottom of the housing 188 is zero or near-zero, and an expanded configuration in which the volume of the fluid chamber is increased. The housing 188 is arranged to surround the outer radial edge portion of the membrane 194 and creates a seal with the membrane 194. The bottom surface of the housing 188 can define a pair of openings which extend into the housing 188 to form internal passageways, providing fluid communication between the fluid chamber and the two one-way valve assemblies 190, 192.

The securing member 186 can be a plate defining a first part 214 extending below a portion of the housing 188 and a second part 212 extending generally upward from the first part and attached to the attachment portion 15 of the upper foot element 14. The first part 214 of the securing member 186 can be connected to the housing 188 in any suitable manner. For instance, the first part of the securing member 186 can be bonded to the front portion of the housing 188. In other embodiments, the first part 214 can secured to the housing 188 via the connector 196 extending through an opening 216 defined in the first part 214.

The securing member 186 can be connected to the attachment portion 15 in any suitable manner but is shown attached via a fastener. The second part 212 can define an aperture for receiving the fastener to connect the securing member 186 to the attachment portion 15 or upper foot element 14.

When the prosthetic foot 4 is in its resting position, the front edge 206 of the housing 188 is engaged with the upper surface of the upper foot element 14 and the pump mechanism 184 is in its original configuration. Upon heel strike, the prosthetic foot 4 moves into expansion, which, in turn, causes the connection unit 22 to push the intermediate foot element 24 away from the engagement surface 210 of the arm member 208. With the prosthetic foot 4 in expansion, the pump mechanism remains in its original configuration.

As the prosthetic foot 4 moves from heel strike through mid-stance and/or toe-off, the prosthetic foot moves into compression. In compression, the connection unit 22 pulls the intermediate foot element 24 toward the upper foot element 14, applying an upward force on the engagement surface 210 of the arm member 208.

This upward force drives the arm member 208 upward, forcing the rear portion 204 away from the securing member 186 and causing the housing 188 to pivot around the connection between the securing member 186 and the housing 188. This pulls the membrane 194 away from the housing 188, driving the pump mechanism 184 toward the expanded configuration. At the end of the stance phase or when the weight of the user is removed from the prosthetic foot 4, the prosthetic foot 4 returns to its resting position and the inherent properties of the housing 188 and/or membrane 194 help move the pump mechanism 184 back toward its original configuration.

Figure 11:
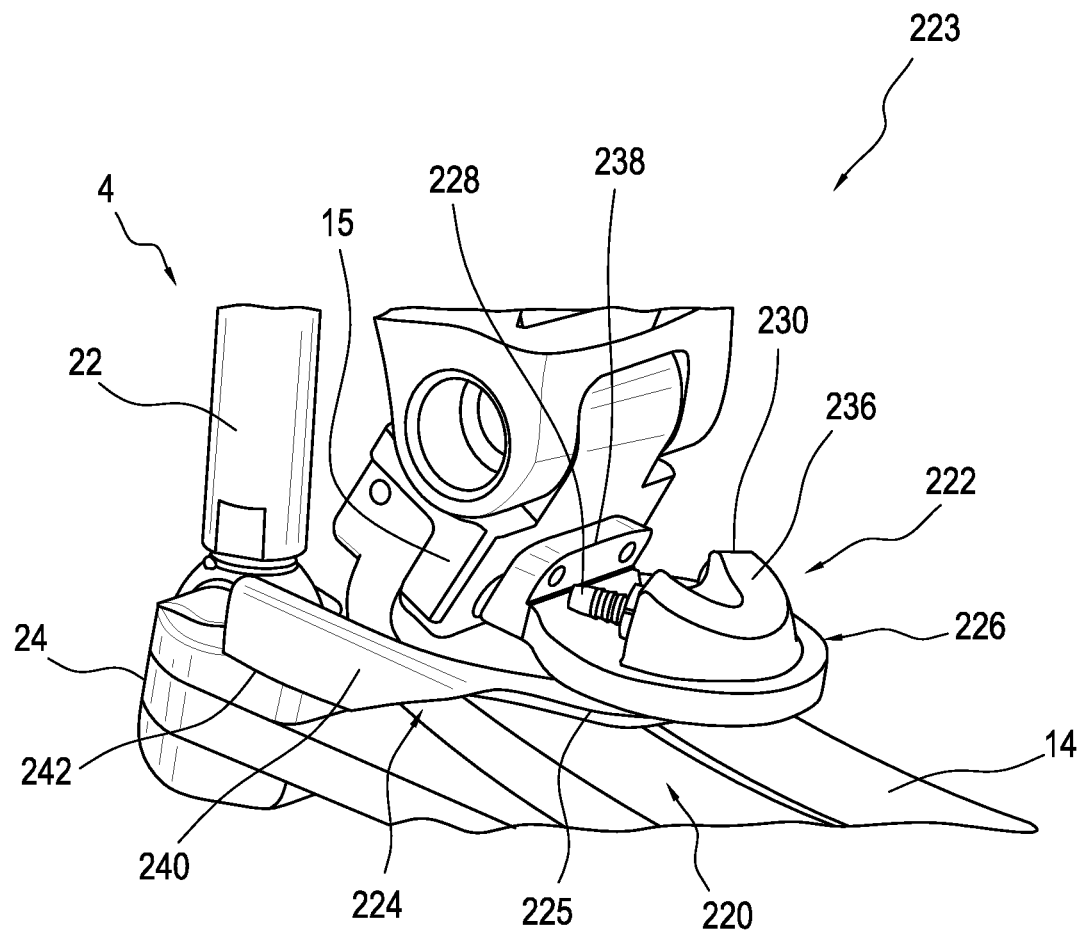
FIG. 11 shows a prosthetic system with a pump system according to another embodiment.
Figure 12:
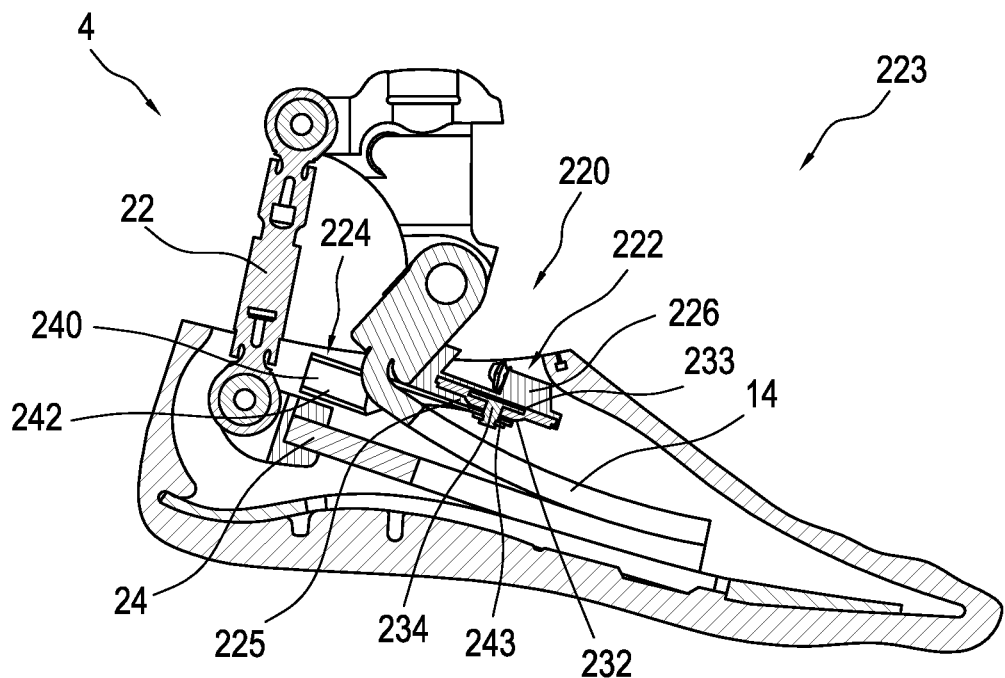
FIG. 12 shows a sectional view of the prosthetic system in FIG. 11 in a first position.
Figure 13:
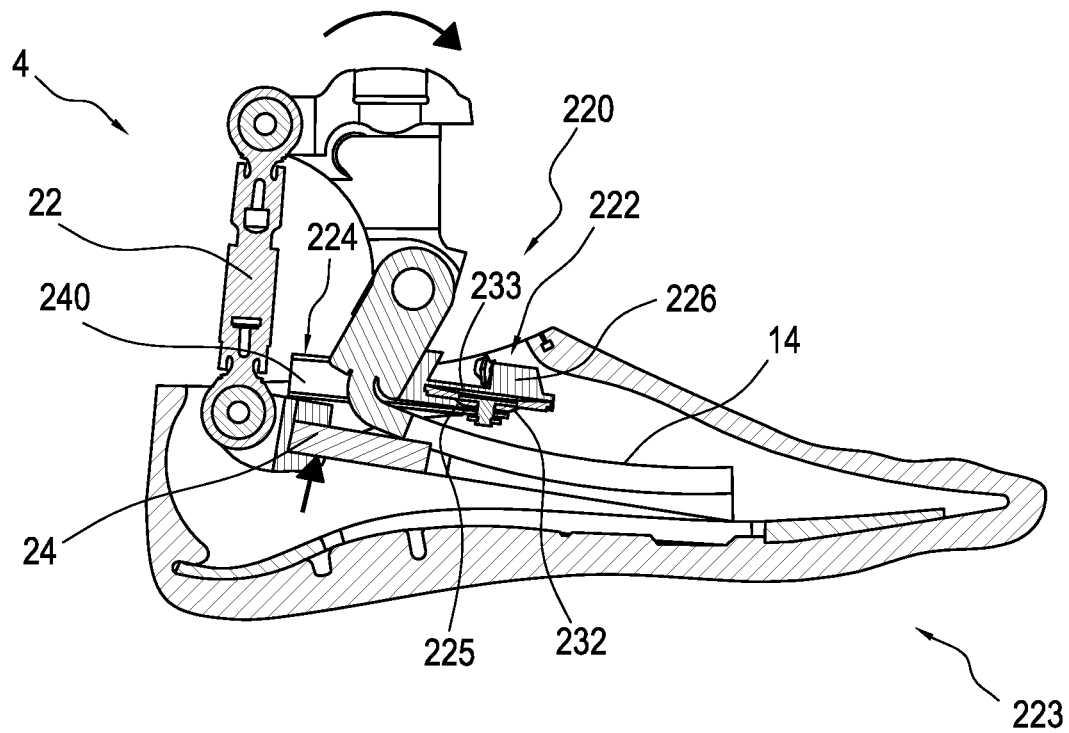
FIG. 13 shows a sectional view of the prosthetic system in FIG. 12 in a second position.

Another embodiment of a prosthetic system 223 comprising a pump system 220 and the prosthetic foot 4 is shown in FIGS. 11-13. This embodiment can be similar to the previously described embodiments except that the pump system has a different construction.

The pump system 220 includes a pump mechanism 222 and an arm member 224 arranged to move or drive the pump mechanism 222 toward at least an expanded configuration (described below) upon movement of the intermediate foot element 24 relative to the upper foot element 14. The pump mechanism 222 includes a housing 226, at least one inlet valve assembly 228, at least one outlet valve assembly 230, a membrane 232 (shown in FIG. 12), and a connector 234 (shown in FIG. 12). The pump mechanism 222 relies upon of the membrane 232 to move between an original configuration in which the volume of a fluid chamber 233 defined between an upper surface of the membrane 232 and the bottom of the housing 226 is zero or near-zero, and an expanded configuration in which the volume of the fluid chamber 233 is increased.

The housing 226 can have a rigid configuration and defines a main portion 236, and a rear portion 238 extending generally upwardly or obliquely from the main portion 236. The housing 226 can be coupled to the attachment portion 15 via at least one fastener. A rear surface of the rear portion 238 can generally complement the front surface of the attachment portion 15. It should be appreciated that the pump mechanism 222 can be a separate add-on module to the prosthetic foot 4. Because the pump mechanism 222 is not integrated into the prosthetic foot 4, failure of the pump mechanism 222 beneficially would not affect the performance of the prosthetic foot 4.

The arm member 224 can be a plate located over the upper foot element 14. A front portion 225 of the plate 224 is connected to the pump mechanism 222 via the connector 234. For instance, the front portion 225 of the plate 224 can define an aperture 243 (shown in FIG. 12) for connecting the plate 224 to the membrane 232 via the connector 234.

The plate 224 has two arms 240 which extend along each side of the prosthetic foot 4 from the plate 224 to the rear area of the intermediate foot element 24. Each arm 240 can include a rear portion defining an engagement surface 242 arranged to engage with the rear portion of the intermediate foot element 24.

Similar to the other embodiments, the pump system 220 utilizes the displacement which occurs between the intermediate foot element 24 and the upper foot element 14 during the gait cycle to move the pump mechanism 222 between its original and expanded configurations.

FIG. 12 shows the prosthetic foot 4 in its resting position. Upon heel strike, the prosthetic foot 4 moves into expansion, which, in turn, causes the connection unit 22 to push the intermediate member 24 away from the engagement surface 242 of the plate 224. With the prosthetic foot 4 in expansion, the pump mechanism remains in its original configuration.

As the prosthetic foot 4 moves from heel strike through mid-stance and/or toe-off, the prosthetic foot 4 moves into compression as seen in FIG. 13. In compression, the connection unit 22 pulls the intermediate foot element 24 toward the upper foot element 14, closing the distance therebetween and applying an upward force on the engagement surface 242 of the plate 224.

The plate 224 then transfers this upward force to the pump mechanism 222, driving the pump mechanism 222 toward the expanded configuration. For instance, the upward force on the engagement surface 242 causes the plate 224 to pivot or rotate at or near the rear portion 238 of the housing 226, rotating the front portion of the plate 224 attached to the membrane 232 away from the housing 226. This forces the pump mechanism 222 toward the expanded configuration.

The pump mechanism 222 can be arranged at various points on the front of the prosthetic foot in combination with different angles of the arms 240 to control the length of the displacement between the original and expanded configurations.

Figure 14:
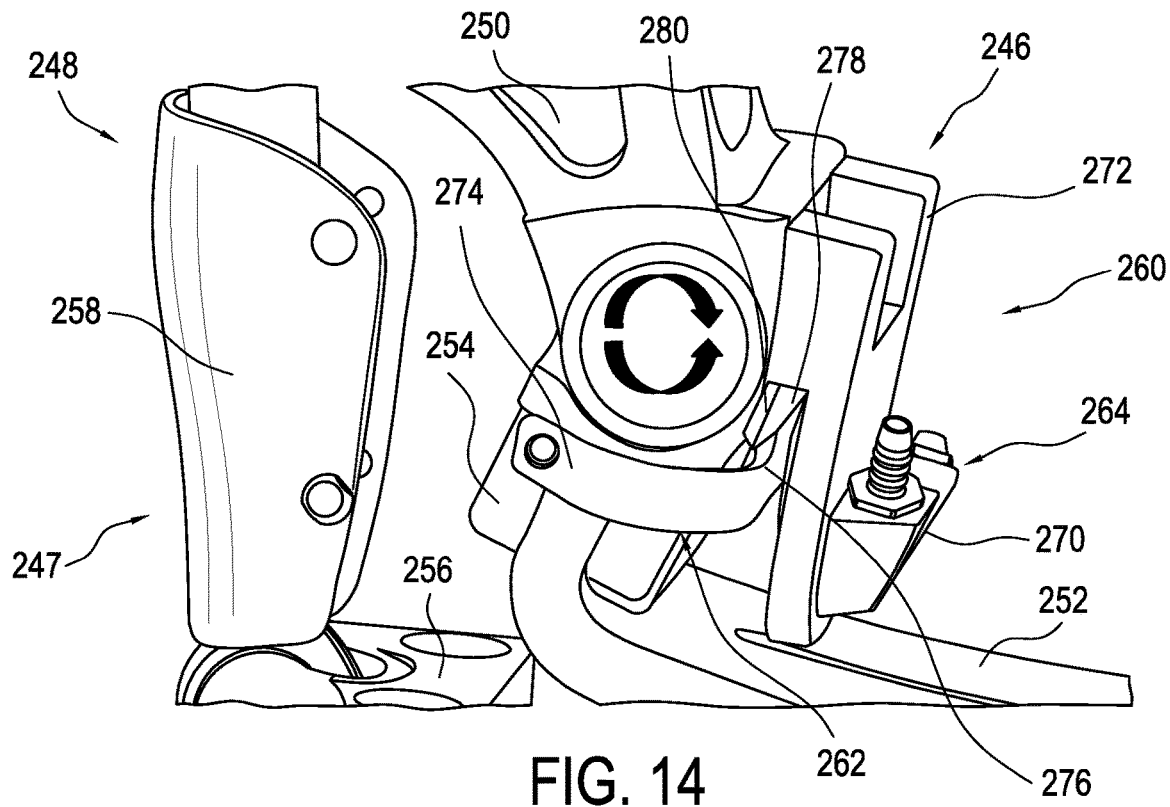
FIG. 14 shows a prosthetic system with a pump system according to another embodiment.

Another embodiment of a prosthetic system 247 comprising a pump system 246 and a prosthetic foot 248 is shown in FIG. 14. This embodiment can be similar to the other embodiments. The prosthetic foot 248 can be similar to other embodiments of the prosthetic foot. For instance, it can include an ankle portion 250 and an upper foot element 252 coupled to the ankle portion 250 via an attachment portion 254. The attachment portion 254 can include or define a bushing or opening through which an axle extends. An intermediate foot element 256 is disposed generally below the upper foot element 252 and attached to the upper foot element 252 at a front portion thereof. A lower foot element can be disposed below the intermediate foot element. A connection unit 258 can extend between the rear of the ankle portion 250 and the rear portion of the intermediate foot element 256. In use, the prosthetic foot 248 can expand and compress.

The pump system 246 includes a pump mechanism 260 coupled to the ankle portion 250 and an arm member 262 coupled to the attachment portion 254 or upper foot element 252. The arm member 262 is arranged to move or drive the pump mechanism 260 toward at least an expanded configuration (described below) upon movement of the intermediate foot element 256 and/or the ankle portion 250 relative to the upper foot element 252. The pump mechanism 260 includes a housing 264 containing two one-way valve assemblies, a membrane 278, and a connector 280. One of the valve assemblies only allows fluid to enter the pump mechanism 246 and the other only allows fluid to be expelled out of the pump mechanism 260. The connector can be attached to the membrane and the arm member 262 and can exhibit any suitable configuration. For instance, the connector may be a fastener or screw.

The housing 264 can include a main portion 270 having a generally cylindrical configuration and a rear portion 272 defining a pair of arms extending from the main portion 270. The rear portion 272 can be secured to the ankle portion 250. A bottom surface of the rear portion 272 can generally complete a portion of the front surface of the ankle portion 250.

Similar to the previously described pump mechanisms, the pump mechanism 260 relies upon deformation of the membrane 278 to move between an original configuration in which the volume of a fluid chamber defined between an upper surface of the membrane 278 and the bottom of the housing 264 is zero or near-zero, and an expanded configuration in which the volume of the fluid chamber is increased. The housing 264 is arranged to surround the outer radial edge portion of the membrane 278 and creates a seal with the membrane 278. The bottom of the housing 264 can define a pair of openings which extend into the housing 264 to form internal passageways to provide fluid communication between the fluid chamber and the two one-way valve assemblies.

The arm member 262 can comprise a resilient or flexible member having a configuration that wraps around a side of the attachment portion 254 to the front of the attachment portion 254. For instance, the arm member 262 defines a first end 274 secured to the side of the attachment portion 250 via a fastener and a second end 276 attached to the connector 280.

Operation of the pump system 246 will now be described according to an embodiment. Upon heel strike, the prosthetic foot 248 moves into expansion as the ankle portion 150 rotates in a first direction (e.g., counter-clockwise direction) and the intermediate foot element 256 moves away from the upper foot element 252. This rotates the pump mechanism 260 on the ankle portion 250 away from the attachment portion 254, which, in turn, causes the arm member 262 to exert a force on the pump mechanism 260. More particularly, this movement of the ankle portion 150 and/or the intermediate foot element 256 causes the arm member 262 on the attachment portion 254 to pull the membrane 278 away from the housing 270, moving the pump mechanism 260 to the expanded configuration.

As the prosthetic foot 248 moves from heel strike through mid-stance and/or toe-off, the ankle portion 250 rotates in a second direction (e.g., clockwise) and the prosthetic foot 248 moves into compression. This rotates the pump mechanism 260 toward the attachment portion 254 and moves the pump mechanism 260 back towards its original configuration. At the end of the stance phase or when the weight of the user is removed from the prosthetic foot 248, the prosthetic foot 248 returns to its resting position and the inherent properties of the arm member 262 help move and/or maintain the pump mechanism 260 in its original configuration.

It should be appreciated that the pump system 246 can be a separate add-on module to the prosthetic foot 248. Because of the location and simple connection of the pump system 246 to the foot, it provides a low-profile design and reduces the likelihood that the pump system 246 will interfere with the performance of the foot.

Figure 15:
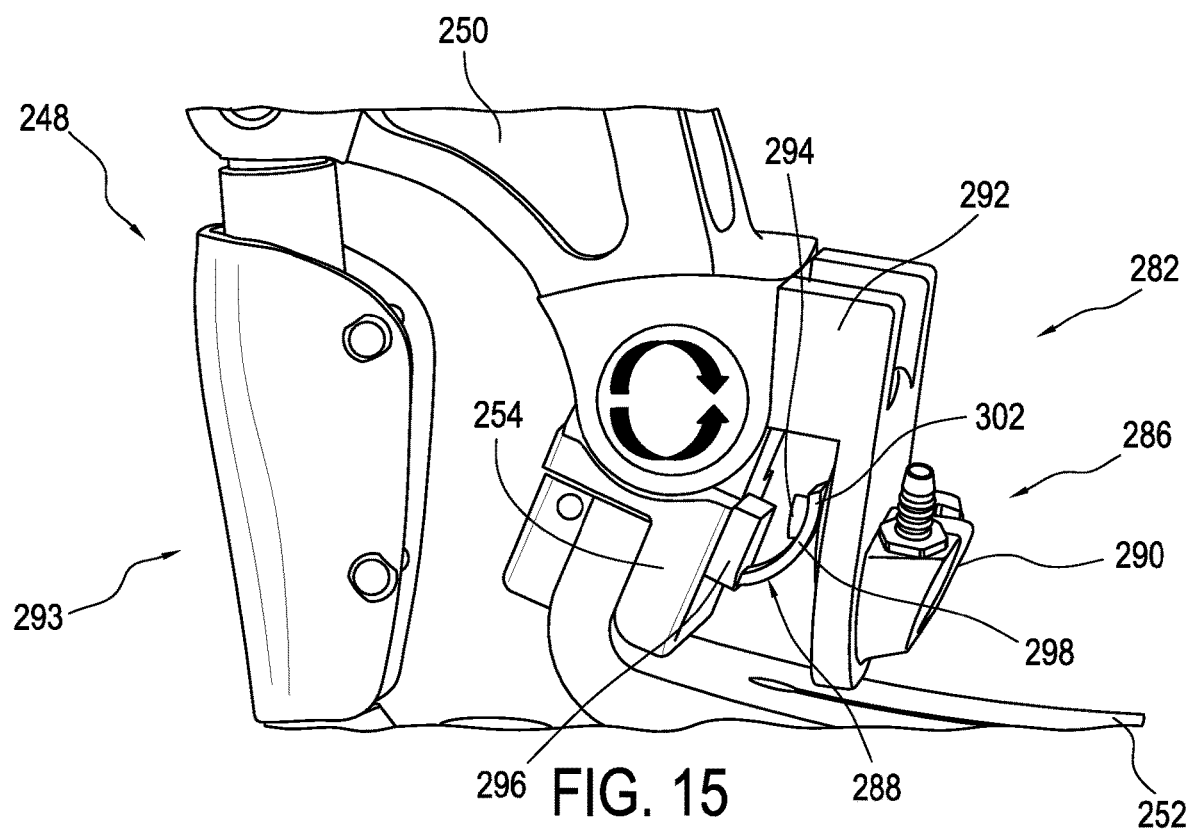
FIG. 15 shows a prosthetic system with a pump system according to another embodiment.

Another embodiment of a prosthetic system 293 comprising a pump system 282 and the prosthetic foot 248 is shown in FIG. 15. This embodiment may be similar to the sixth embodiment except that the pump system 282 includes a housing 286 and an arm member 288 having a different construction.

The pump mechanism 282 can be coupled to the ankle portion 250 and the arm member 288 can be coupled to the attachment portion 254 or upper foot element 252. The housing 286 can include a main portion 290 having a generally cylindrical configuration and a rear portion 292 defining a pair of arms extending from the main portion 290. The rear portion 292 can be secured to the ankle portion 250. Each of the arms can have a portion exhibiting a width greater than the main portion 290, creating a gap between the bottom surface of the housing 286 and the attachment portion 254 of the foot 248.

The arm member 288 can comprise a resilient member extending between the front surface of the attachment portion 254 and a connector 294 of the pump mechanism 282. For instance, the arm member 288 can include a rear end portion including a mounting member 296 attached to the front surface of the attachment portion 254 and a front end portion 298 defining an opening for attaching the arm member 288 to a membrane 302 of the pump mechanism 282.

Operation of the pump system 282 will now be described according to an embodiment. Upon heel strike, the prosthetic foot 248 moves into expansion as the ankle portion 150 rotates in a first direction (e.g., counter-clockwise direction) and the intermediate foot element 256 moves away from the upper foot element 252. This rotates the pump mechanism 282 on the ankle portion 250 away from the attachment portion 254, which, in turn, causes the arm member 288 on the attachment portion 254 to pull the membrane 302 away from the housing 286 and drive the pump mechanism 282 toward the expanded configuration.

As the prosthetic foot 248 moves from heel strike through mid-stance and/or toe-off, the ankle portion 250 rotates in a second direction (e.g., clockwise) and the prosthetic foot 248 moves into compression. This rotates the pump mechanism 282 toward the attachment portion 254 and moves the pump mechanism 282 back towards its original configuration.

Figure 16:
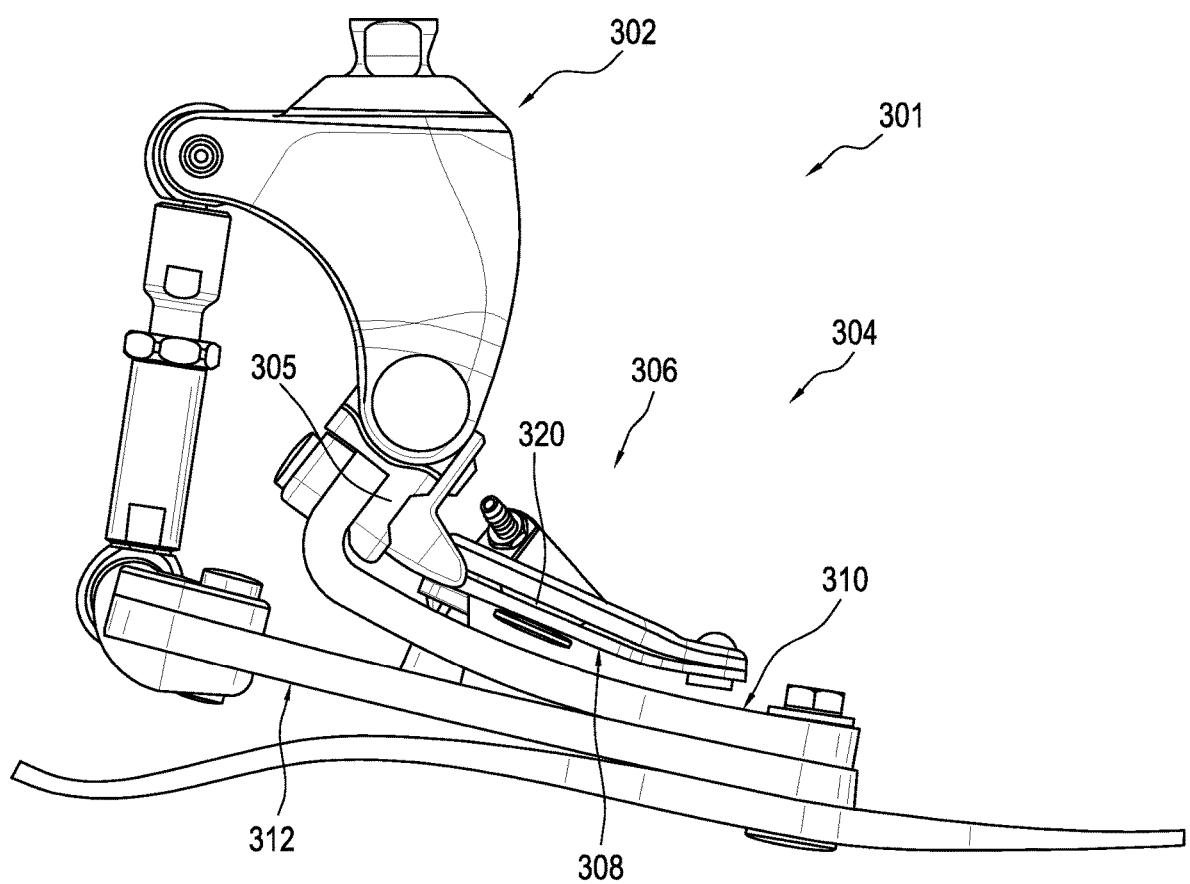
FIG. 16 shows a prosthetic system with a pump system according to another embodiment.
Figure 18:
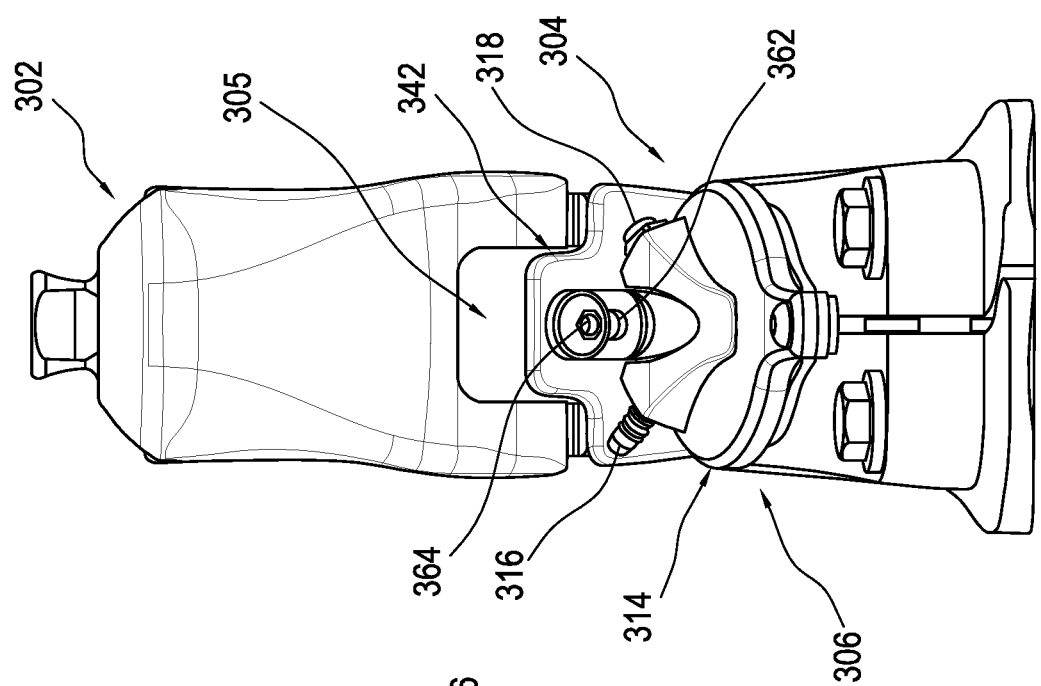
FIG. 18 shows a front view of the prosthetic system and pump system of FIG. 16.
Figure 17:
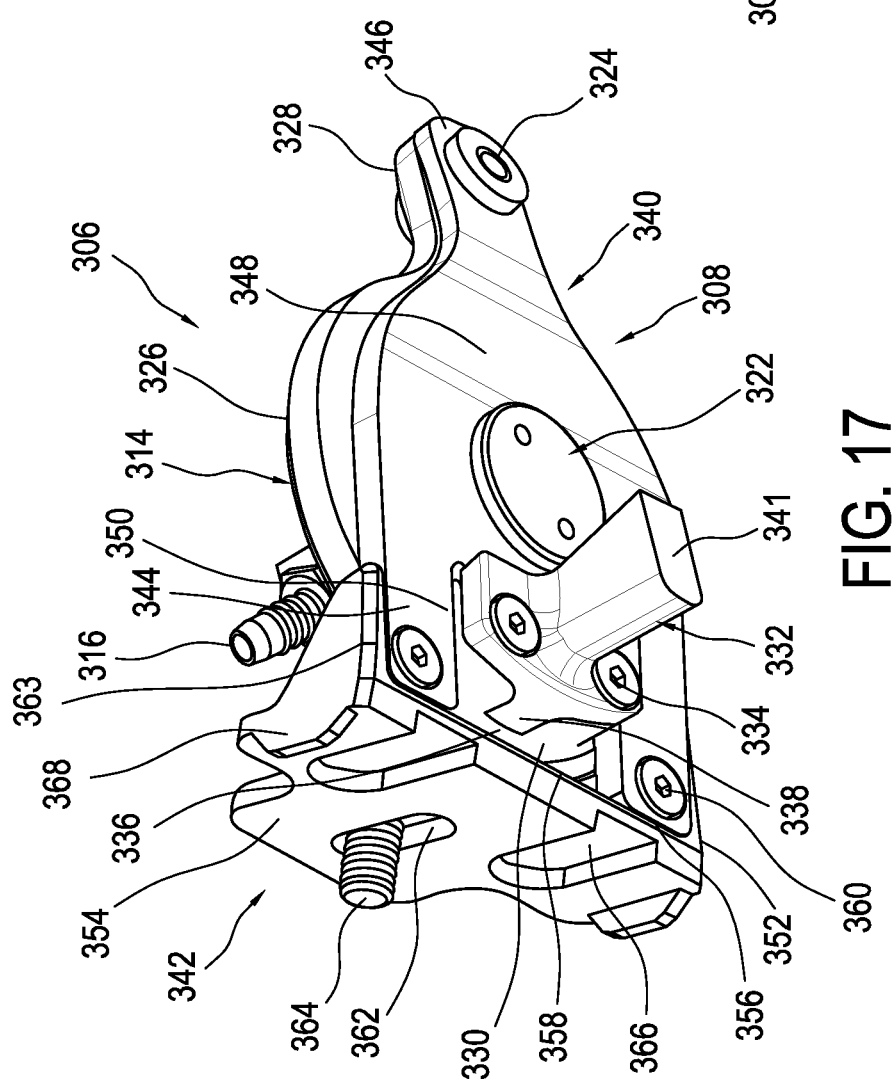
FIG. 17 shows the pump system of FIG. 16 removed from the prosthetic system.

Another embodiment of a prosthetic system 301 is shown in FIGS. 16-18. This embodiment can be similar to the previous embodiments described. For instance, the prosthetic system 301 includes a prosthetic foot 302 and a pump system 304. The pump system 304 includes a pump mechanism 306 and a securing member 308. The pump mechanism 306 is attached to the securing member 308 and situated above an upper foot element 310 of the prosthetic foot 302. The pump mechanism 306 is operably connected to an intermediate foot element 312 of the prosthetic foot 302.

Referring to FIGS. 17 and 18, the pump mechanism 306 includes a housing 314 containing two one-way valve assemblies 316, 318, a membrane 320 (shown in FIG. 16), and a connector 322. The valve assembly 316 only allows fluid to enter the pump mechanism 306 which can be in fluid communication with the cavity of a socket. The valve assembly 318 only allows fluid to be expelled out of the pump mechanism 306, preferably to atmosphere. The connector 322 can be any suitable connector. For instance, it can include an upper radial flange embedded in the membrane 320, a lower radial flange below the membrane 320, and a shaft portion extending between the upper and lower flanges.

The housing 314 can be coupled to the securing member 308 via at least one fastener 324 situated at the front portion of the housing 314 and the securing member 308. The housing 314 can have a rigid configuration. The housing 314 defines a main portion 326, a front portion 328, and a rear portion 330 opposite the front portion 328. The front portion 328 can have an elongate configuration and extend forwardly over or along an upper surface of the securing member 308.

The rear portion 330 of the housing 314 can be associated with an arm member 332 arranged to move or drive the pump mechanism 306 toward at least an expanded configuration upon movement of intermediate foot element 312 and/or the ankle portion 250. The arm member 332 can extend generally downward from the housing 314 and can be integral to or separate from the housing 314. In the illustrated embodiment, the arm member 332 can be selectively secured to the rear portion 330 of the housing 314 via at least one fastener 334 respectively positioned in at least one fastener hole defined by the arm member 332 and at least one fastener hole defined in the bottom surface of the rear portion 330. Because the arm member 332 can be easily removed from the housing 314 and replaced, the length, stiffness, and/or shape of the arm member 332 can be advantageously adjustable or customizable without having to replace the entire housing 314.

The bottom surface of the rear portion 330 can define a keyway 336 and a corresponding key 338 can be defined on an upper surface of the arm member 332. When the arm member 332 is connected to the housing 314, the key 338 slides into the keyway 336 defined by the housing 314. This prevents relative rotation between the arm member 332 and the housing 314. It also provides a solid connection between the arm member 332 and the housing 314 by increasing the contact surface area between the arm member 332 and the housing 314. It further aligns the fastener holes, facilitating assembly and/or disassembly of the pump mechanism 306.

The arm member 332 has an upper head portion for connection to the housing 314 and a shaft portion extending downwardly from the head portion. The shaft portion has a lower end defining an engagement surface 341 arranged to engage with an upper surface of the intermediate foot element 312. The shaft portion of the arm member 332 can include a width or a cross-sectional area that increases toward the engagement surface 341, providing a more solid connection between the arm member 332 and the intermediate foot element 312.

Similar to the embodiments of the pump mechanism previously described, the pump mechanism 306 relies upon deformation of the membrane 320 to move between an original configuration in which the volume of a fluid chamber defined between the top surface of the membrane 320 and the bottom of the housing 314 is zero or near-zero, and an expanded configuration in which the volume of the fluid chamber is increased. The housing 314 can be arranged to surround the outer radial edge portion of the membrane 320 and creates a seal with the membrane 320. The bottom surface of the housing 314 can define a pair of openings which extend into the housing 314 to form internal passageways, providing fluid communication between the fluid chamber and the two one-way valve assemblies 316, 318.

The securing member 308 can include a plate member 340 and a backing portion 342. Optionally, the backing portion 342 and the plate member 340 can be made of different materials. For example, the plate member 340 can be made of carbon fiber cloth and the backing portion 342 can be made of metal, plastic, combinations thereof, or any other suitable material, facilitating production. Further, because the securing member 308 includes a two part construction, the length, curvature, and/or shape of the plate member 340 or backing portion 342 can be beneficially adjustable or customizable without having to replace the entire securing member 308.

The plate member 340 can include a rear portion 344, a front portion 346, and a middle portion 348 extending between the rear and front portions 344, 346. The plate member 340 can have any suitable shape but is shown having a width that tapers from the middle portion 348 toward the front portion 346 such that the front portion 346 is narrower than the middle portion 348.

The front portion 346 can define an aperture for receiving the fastener 324 to connect the plate member 340 to the front portion of the housing 314. The middle portion 348 can define an aperture for connecting the plate member 340 to the connector 322. A slot or notch 350 is formed in the terminal edge of the rear portion 344 that allows the arm member 332 to extend through the plate member 340 toward the intermediate foot element 312 of the foot 302. The rear portion 344 can define a pair of apertures on opposing sides of the notch 350.

The backing portion 342 includes a base 352 and a back member 354. The bottom surface of the base 352 defines a seat 356 arranged to accommodate the rear portion 344 of the plate member 340 when the plate member 340 is attached to the backing portion 342. This beneficially limits or prevents the plate member 340 from sliding sideways off of the backing portion 342. A slot or notch 358 is defined in the base 352. The slot 358 can accommodate a portion of the housing 314 and allow the arm member 332 to extend through the base 352.

The base 352 defines a pair of apertures in the seat 356 corresponding to the apertures on the plate member 340 for receiving one or more fasteners 360 to attach the plate member 340 to the backing portion 342. The seat 356 can be in part defined by a pair of side arms 363 defined on the backing portion 342 extending along a portion of the sides of the plate member 340. This helps align the fastener apertures formed in the base and plate member 340, facilitating assembly.

The back member 354 can extend generally upward from a rear end of the base 352. The back member 354 can be generally perpendicular to the base 352 or oblique relative to the base 352. The back member 354 can define an aperture 362 for receiving a fastener to connect the backing portion 342 to the attachment portion 305 or upper foot element of the foot 302.

It should be appreciated that the pump system 304 can include one or more features for adjusting the sensitivity of the pump mechanism. For example, as seen in FIGS. 17 and 18, the aperture 362 can have an elongate configuration for receiving the fastener 364. This allows the fastener 364 to slide up and down within the aperture 362 such that the position of the pump system 304 relative to the upper foot element 310 and/or intermediate foot element 312 can be adjusted before a user tightens the fastener 364 to securely attach the securing member 308 to the attachment portion of the upper foot element 310.

The height adjustability of the pump system 304 on the attachment portion 305 can in turn vary the sensitivity of the pump mechanism 306, which may depend on user activity level, weight, and/or other factors. For instance, by adjusting the height of the pump system 304 on the attachment portion 305, the amount and/or period of force applied to the arm member 332 may be adjusted, varying the sensitivity of the pump mechanism 306 to action of the prosthetic foot 302, advantageously making the pump mechanism 306 customizable to the needs of the user or desires of a clinician.

In other embodiments, the notch 350 and/or the apertures in the plate member 340 for receiving the connector 322 and the fastener 324 can have an elongate configuration such that the pump mechanism 306 can slide forward and/or backward along the plate member 340 relative to the attachment portion 305. Independent of or in combination with the height adjustability, this axial or longitudinal adjustability of the pump system 304 along the plate member 340 can vary the sensitivity of the pump mechanism 306. For instance, by moving the pump mechanism 306 forwardly toward the front of the foot 302 along the plate member 340, the amount of relative movement between the intermediate foot element 312 and the upper foot element 310 required to actuate the pump mechanism 306 is reduced because of the tapering separation between the intermediate foot element 312 and the upper foot element 310, varying the sensitivity of the pump mechanism 306 to action of the foot 302.

According to a variation, the lower end of the arm member 332 can include a wedge or tapered shape arranged to more easily advance between the intermediate foot element 312 and the upper foot element 310.

In yet other embodiments, the aperture in the housing 314 for receiving the fastener 324 can have an elongate configuration similar to the aperture in the plate member 340 such that the distance between the arm member 332 and the connection of the housing 314 to the plate member 340 is adjustable. This in turn permits the magnitude of the moment generated as the arm member 332 pushes on the housing 314 to be adjusted, varying the sensitivity of the pump mechanism 306.

The rear surface of the back member 354 can generally complement the front surface of the attachment portion 305. As seen, the rear surface of the back member 354 can define one or more grooves 366 arranged to accommodate one or more projections associated with the attachment portion 305 as the height of the pump system 304 relative to the intermediate foot element is adjusted.

Optionally, the back member 354 can include one or more alignment features arranged to help align the securing member 308 on the attachment portion 305. For example, the back member 354 can define a pair of opposing members 368 protruding rearwardly from the sides of the back member 354 and arranged to engage or extend along opposing sides of the attachment portion 305 when the securing member 308 is positioned on the attachment portion 305. This beneficially helps align the fastener aperture 362 on the back member 354 and a fastener aperture on the attachment portion 305, facilitating connection and/or removal of the securing member 308 from the foot 302. It also helps limit or prevent relative movement or rotation between the back member 354 and the attachment portion 305.

Another embodiment is shown in FIGS. 19 and 20. This embodiment can include a pump mechanism 370 arranged to be operably connected to a prosthetic foot such that action of the prosthetic foot can actuate the pump mechanism 370. The pump mechanism 370 can be a separate add-on module to the prosthetic foot.

The pump mechanism 370 can be similar to the previous embodiments described. For example, the pump mechanism 370 includes a housing 372 containing one or more valve assemblies, a membrane 374, and a connector 376. The one or more valve assemblies can include a one-way valve, also referred to as a check valve. A preferred type of one-way valve used is a duckbill valve. It should be appreciated however that other types of one-way valves are possible.

The one or more valve assemblies can include a valve assembly arranged to only allow fluid to enter the pump mechanism 370. The valve assembly can be in fluid communication with the cavity of a prosthetic socket. When the volume of the pump mechanism 370 increases, fluid (e.g., air) can be drawn out from the socket via the valve assembly. The one or more valve assemblies can include another valve assembly arranged to only allow fluid to be expelled out of the pump mechanism 370, preferably to atmosphere.

The housing 372 can have a rigid configuration. The housing 372 can have any shape but is shown having a generally cylindrical shape. The bottom surface of the housing 372 defines a cavity 378 that is provided with an undercut circumferential groove 380 between an open end of the cavity 378 and a closed bottom 382 of the cavity 378. An outer radial edge portion of the membrane 374 can be situated in the circumferential groove 380 such that a seal is formed between the membrane 374 and the housing 372.

Optionally, an adhesive can be applied between the housing 372 and the outer radial edge portion of the membrane 374, increasing the sealing effect. The bottom 382 can define two openings which extend into the housing 372 to form internal passageways providing fluid communication between a fluid chamber defined below and the one or more valve assemblies.

The pump mechanism 370 is movable between an original configuration in which the volume of a fluid chamber 384 defined between the top surface of the membrane 374 and the bottom 382 of the cavity 378 is zero or near-zero, and an expanded configuration in which the volume of the fluid chamber 384 is increased. The bottom 382 of the cavity 378 can substantially complement the top surface of the membrane 374. Both the bottom 382 of the cavity 378 and the top surface of the membrane 374 can be generally flat.

The membrane 374 may have any desired shape, but is shown having a generally circular or elliptical shape. The membrane 374 can be operatively attached at or near its center to the connector 376 while the outer radial edge portion of the membrane 374 is attached to the housing 372 such that when the connector 376 pulls the membrane away from the housing 372, for example, a pocket forms in a middle area of the membrane 374 due to the deformation of the membrane 374. The formation of the pocket increases the volume of the fluid chamber 384. The pump mechanism 370 thus uses a compliant membrane to create suction.

The connector 376 can have an upper portion 386 embedded in the membrane 374, a lower portion 388 below the membrane 374, and a shaft portion 390 extending between the upper and lower portions 386, 388. Optionally, the connector 376 may be of a two-piece construction such that the lower portion 388 can be threadedly removed from the upper portion 386 in the membrane 374. At least the upper portion 386 of the connector 376 can include one or more ferromagnetic materials such as steel, iron, cobalt, or other suitable metal. The upper portion 386 may extend substantially into the membrane 374.

The pump mechanism 370 can include a closure-assist mechanism 392 arranged to bias or move the pump mechanism 370 toward its original configuration and/or maintain it therein. In the illustrated embodiment, the closure-assist mechanism 392 comprises a closure element 392 secured within a cavity or an opening 394 defined in the bottom 382 of the cavity 378. The closure element 392 can include one or more magnetic materials such that magnetism can attract or pull the ferromagnetic upper portion 386 of the connector 376 toward the bottom 382 of the cavity 378, which, in turn, attracts or pulls the membrane 374 toward the bottom 382. It will be appreciated that in other embodiments the closure element 392 can include ferromagnetic materials and the connector 376 can be a magnet, or both may include magnetic materials. In other embodiments, the closure element 392 can be omitted. For instance, the housing 372 may include one or more magnetic materials.

When the connector 376 exerts an expansion or opening force on the membrane 374 sufficient to overcome the closure force between the closure element 392 and the upper portion 386 of the connector 376, the pump mechanism 370 can move toward the expanded configuration as the expansion force pulls a portion of the membrane 374 away from the bottom 382 of the cavity 378, causing deformation of the membrane 374 and an increase in volume of the fluid chamber 384. This increase in volume of the fluid chamber 384 can draw fluid into the fluid chamber 384 from a socket through the one or more valve assemblies. The housing 372 may be formed of metal such as stainless steel, carbon fiber, plastic or any other material which would provide sufficient strength to resist deformation when pulled away from the membrane 374.

Once the expansion force is reduced or removed, the pump mechanism 370 returns toward its original configuration as the membrane 374 returns toward the bottom 382 of the cavity 378 and fluid within the fluid chamber 384 is expelled out of the pump mechanism 370. The closure force between the upper portion 386 of the connector and the closure element 392 can move the membrane 374 to its original position on the bottom 382 on the cavity 378. This beneficially helps expel fluid from the fluid chamber 384 as its volume is decreased to zero or near-zero. It also advantageously helps maintain the pump mechanism 370 in its original configuration. It can also help maintain the membrane 374 sealed against the housing when no force or smaller forces are exerted on the membrane 374 by the connector and/or the prosthetic foot. Further, the closure force can be customized based on the individual needs of the user. For example, the magnetic strength of the closure element 392 can be selected to vary the closure force.

Another embodiment is shown in FIGS. 21-23. This embodiment can include a pump mechanism 396 arranged to be operably connected to a prosthetic foot such that action of the prosthetic foot moves the pump mechanism 396 between an original configuration and an expanded configuration to create an elevated vacuum. The pump mechanism 396 can be a separate add-on module to the prosthetic foot.

The pump mechanism 396 can be similar to the previous embodiments described in many respects. For instance, the pump mechanism 396 includes a housing 398, a membrane 402, and a connector 404. The housing 398 can include at least one valve assembly 406 arranged to only allow fluid to enter the pump mechanism 396 and can be in fluid communication with the cavity of a prosthetic socket. The at least one valve assembly 406 can include a one-way valve or check valve. A preferred type of one-way valve used is a duckbill valve however other types of one-way valves are possible. When the volume of the pump mechanism 396 increases, fluid (e.g., air) can be drawn out from the socket via the valve assembly 406.

The housing 398 can have a rigid configuration. The housing 398 can include an upper member 408 and a base member 410. The upper member 408 can have any shape but is shown having a generally cylindrical shape with a body portion. The bottom surface of the upper member 408 can define an opening 412 which extends into the upper member 408 to form an internal passageway providing fluid communication between a fluid chamber defined below and the at least one valve assembly 406.

The membrane 402 is arranged to engage the bottom of the upper member 408 such that a seal can be created therebetween. The membrane 402 may have any desired shape, but is shown having a generally circular configuration. The bottom surface of the membrane 402 can have a contour tapering toward the center.

The pump mechanism 396 is movable between an original configuration in which the volume of a fluid chamber 414 defined between the top surface of the membrane 402 and the bottom of the upper member 408 is zero or near-zero, and an expanded configuration in which the volume of the fluid chamber 414 is increased. The bottom of the upper member 408 can substantially complement the top surface of the membrane 402. Both the bottom of the upper member 408 and the top surface of the membrane 402 can be generally flat.

The connector 404 can have an upper portion 416 embedded in the membrane 402 and a shaft portion 418 extending downwardly from the upper portion 416. The upper portion 416 may extend substantially into the membrane 402. In some embodiments, the connector 404 can include a lower portion comprising a fastener arranged to be threadedly removable from the connector 404.

The membrane 402 can be operatively attached at or near its center to the connector 404. As disclosed in more detail below, when the connector 404 pulls the membrane 402 away from the upper member 408 a pocket forms in the middle area of the membrane 402 due to the deformation of the membrane 402. The formation of the pocket increases the volume of the fluid chamber 414. The pump mechanism 396 thus uses a compliant membrane to create suction.

The base member 410 may have any desired shape, but is shown having a circular shape defining an interior opening 420. The outer edge portion of the bottom of the membrane 402 rests on the portion of the base member 410 surrounding the opening 420 and a center portion of the membrane 402 and the shaft portion 418 are situated within or extend through the opening 420. The opening 420 can be dimensioned and configured such that the base member 410 does not undesirably interfere with movement of the membrane 402 and connector 404 during operation of the pump mechanism 396.

A plurality of connecting portions 422 are circumferentially spaced around the outer periphery of the base member 410, defining spaces or gaps 430 between the connecting portions 422. Each connecting portion 422 includes a generally upright part 424 and a flange part 426 extending radially inward from the top of the upright part 424. The flange part 426 is arranged to extend over and engage an upper surface of the upper member 408 such that the membrane 402 can be retained or secured between the upper member 408 and the base member 410.

When the connector 404 exerts a force on the membrane 402 in a direction away from the bottom of upper member 408, the pump mechanism 396 moves toward the expanded configuration as the connector 404 pulls a center portion of the membrane 402 away from the bottom of the upper member 408 while the outer edge portion of the membrane 402 remains engaged with the upper member 408, causing deformation of the membrane 402 and an increase in the volume of the fluid chamber 414. This increase in volume of the fluid chamber 414 can draw fluid into the pump mechanism 396 through the valve assembly 406.

Once the force is reduced or removed from the membrane, the pump mechanism 396 can return toward its original configuration as the membrane 402 returns toward the bottom of the upper member 408. This closing movement decreases the volume of the fluid chamber 414, which, in turn, increases the pressure within the fluid chamber 414 until the seal between the upper surface of the membrane 402 and the upper member 408 is broken, allowing fluid in the fluid chamber 414 to be expelled out of the sides of the pump mechanism 396 through the gaps 430 between the connecting portions 422. In other words, the fluid in the fluid chamber 414 can escape from between the upper member 408 and the membrane 402 out the side of the housing 398.

The membrane 402 can be elastomeric and can use at least in part its material properties to naturally or elastically return to its original position on the bottom of the upper member 408. It will be appreciated that the prosthetic device may include arm or plate operatively connected to the prosthetic foot and arranged to bias or force the membrane 402 toward the bottom of the upper member 408, helping to keep the membrane 402 sealed against the upper member 408. In other embodiments, the pump mechanism 396 can include a closure-assist mechanism such as a spring or metal clip to bias or help return the membrane 402 toward the bottom of the upper member 408. For instance, the pump mechanism 396 can include a resilient member that engages the upper member 408 and the membrane 402 and/or the connector. The resilient member biases the membrane 402 toward the bottom of the upper member 408. The resilient member can comprise a generally u-shaped member, a torsion spring, a torsion bar, or any other suitable member.

Because the pump mechanism 396 can expel fluid, preferably to atmosphere, without the use of a second valve assembly or a second port in the housing, the pump mechanism 396 is beneficially lighter and easier to manufacture and maintain. Further, the structure of the pump mechanism 396 is simpler and helps reduce resistance to air flow out of the pump mechanism 396. Moreover, the point at which the buildup of pressure within the fluid chamber 414 selectively breaks the seal between the membrane 402 and the upper member 408 can be any suitable pressure and/or can be customized based on the individual needs of the user. This pressure can be selected to set by a user, a clinician, or a medical professional.

Figure 24:
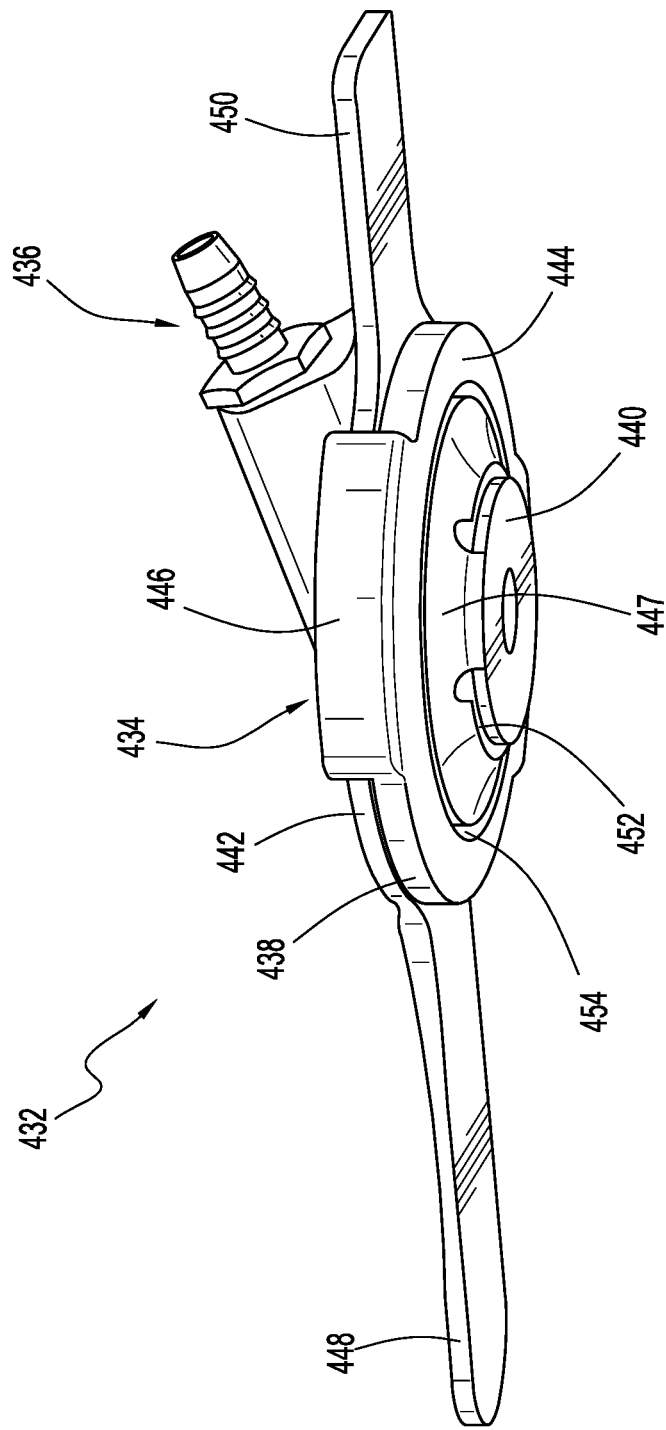
FIG. 24 shows a pump mechanism according to another embodiment.

Another embodiment is shown in FIG. 24. This embodiment can include a pump mechanism 432 similar to the pump mechanism 396 except that the upper member is integral to the base member. The pump mechanism 432 includes a housing 434 containing a valve assembly 436, a membrane 438, and a connector 440 embedded in part in the membrane 438. The valve assembly 436 is arranged to only allow fluid to enter the pump mechanism 432. The housing 434 includes an upper member 442 and a base member 444 spaced from the upper member 442.

The membrane 438 can be disposed in the space between the upper member 442 and the base member 444 and arranged to engage the bottom of the upper member 442 such that a seal can be formed therebetween. One or more connecting portions 446 connect the upper member 442 to the base member 444. The connecting portions 446 can be integral to the upper member 442 and the base member 444.

In the illustrated embodiment, the upper member 442 can include a first elongate portion 448 extending radially from a body portion of the upper member 442 in a first direction and a second elongate portion 450 extending radially from the body portion in a second direction. The elongate portions can advantageously help move the pump mechanism 432 between the original and expanded configurations. The base member 444 can define an opening 452 arranged to allow a portion of the connector 440 and membrane 438 to pass through the base member 444.

The pump mechanism 432 relies upon deformation of the membrane 438 to move between an original configuration in which the volume of a fluid chamber defined between the top surface of the membrane 438 and the bottom of the upper member 442 is zero or near-zero, and an expanded configuration in which the volume of the fluid chamber increases.

In use, when the connector 440 exerts a force on the membrane 438 away from the bottom of the upper member 442, the pump mechanism 432 moves toward the expanded configuration as the volume of a fluid chamber increases. This increase in volume of the fluid chamber can draw fluid into the pump mechanism 432 through the valve assembly 436.

Once the force is reduced or removed from the membrane, the pump mechanism 432 returns toward its original configuration as the membrane 438 returns toward the bottom of the upper member 442. This closing movement decreases the volume of the fluid chamber, which, in turn, increases the pressure in the fluid chamber until the seal between the upper surface of the membrane 438 and the upper member 442 is broken, allowing fluid in the fluid chamber to be expelled out of the sides of the pump mechanism 432 between the connecting portions 446.

The base member 444 can include at least one closure-assist feature arranged to help move the pump mechanism 432 toward its original configuration. For instance, the base member 444 can define a closure-assist mechanism 447 comprising a ring portion 447 having a conical configuration with a free edge portion defining the opening 452, and arranged to bias or force the membrane 438 toward the bottom of the upper member 442. The bottom of the base member 444 can define a recess 454 extending around the ring portion 447. This beneficially increases the flexibility of the ring portion 447 relative to the remainder of the base member 444.

As the connector 440 forces the membrane 438 away from the upper member 442, the force of the membrane on the ring portion 447 can flex the free edge portion in a direction away from the upper member 442, storing mechanical energy in the ring portion 447. When the force on the membrane 438 is removed or reduced, the stored energy or resilient properties of the ring portion 447 can force the free edge portion back toward the bottom of the upper member 442, which, in turn, moves the membrane 438 toward the bottom of the upper member 442.

This beneficially helps expel fluid from the fluid chamber as its volume is decreased to zero or near-zero. The closing force of the ring portion 447 also advantageously helps maintain the pump mechanism 432 in its original configuration when no force or smaller forces are exerted on the membrane 438 by the connector and/or the prosthetic foot. The closing force can also help keep the membrane 438 sealed against the bottom of the upper member 442.

Another embodiment of the prosthetic device is shown in FIGS. 25-27. This embodiment can include a pump mechanism 456 arranged to be operably connected to a prosthetic foot such that action of the prosthetic foot moves the pump mechanism 456 between an original configuration and an expanded configuration to create an elevated vacuum.

The pump mechanism 456 can include many of the same features as the pump mechanism embodiments previously described. For instance, the pump mechanism 456 includes a housing 458, a membrane 460, and a connector 462. In other embodiments, the pump mechanism 456 can include an arm member arranged to move the pump mechanism toward an expanded configuration described below.

The housing 458 can include at least one valve assembly 464 arranged to only allow fluid to enter the pump mechanism 456 and can be in fluid communication with the cavity of a prosthetic socket. The at least one valve assembly 464 can include a one-way valve or check valve. A preferred type of one-way valve used is a duckbill valve however other types of one-way valves are possible. When the volume of the pump mechanism 456 increases, fluid can be drawn out from the socket via the valve assembly 464.

The housing 458 can include an upper member 466 and a base member 468. The upper member 466 is shown having a generally cylindrical shape with a body portion but can have any suitable shape. The bottom surface of the upper member 466 can define an opening which extends into the upper member 466 to form an internal passageway providing fluid communication between a fluid chamber defined below and the at least one valve assembly 464.

The membrane 460 is arranged to engage the bottom of the upper member 466 such that a seal can be formed therebetween. The membrane 460 may have any suitable shape. For instance, the membrane 460 can be generally cylindrical with a lower conical contour.

Similar to the other embodiments, the pump mechanism 456 is movable between an original configuration in which the volume of a fluid chamber 470 defined between the top surface of the membrane 460 and the bottom of the upper member 466 is zero or near-zero, and an expanded configuration in which the volume of the fluid chamber 470 is increased. The bottom of the upper member 466 can substantially complement the top surface of the membrane 460 and is arranged to form a seal between the upper member 466 and the membrane 460. Both the bottom of the upper member 466 and the top surface of the membrane 460 can be generally flat.

As seen, the connector 462 can include an upper portion 472 embedded in the membrane 460 and a shaft portion 474 extending downwardly from the upper portion 472. The upper portion 472 may extend substantially into the membrane 460. Optionally, the connector 462 can include a lower portion comprising a fastener arranged to be threadedly removable from the connector 462.

The connector 462 can be attached at or near a center of the membrane 460. As described in more detail below, when the connector 462 pulls the membrane 460 away from the upper member 466 a pocket forms in the center or middle area of the membrane 460 due to the deformation of the membrane 460. The formation of the pocket increases the volume of the fluid chamber 470. The pump mechanism 456 thus uses a compliant membrane to create suction.

The base member 468 can include an open cavity 476 having a peripheral internal wall. The cavity 476 may have any desired shape, but is shown having a generally cylindrical shape. The cavity 476 is arranged so that the top opening is located at or near the top of the base member 468 and a closed bottom 478 located at or near the bottom of the bottom of the base member 468. An aperture 480 can be defined in the closed bottom 478, arranged to allow the lower portion of the connector 462 to extend through the bottom 478.

The cavity 476 can include an upper cavity area adjacent to the top opening and a lower cavity area located towards the closed bottom. The upper and lower cavity areas can be generally concentric. The base member 468 can be formed of any of the materials previously described.

The upper cavity area can define an undercut circumferential groove 482 in the peripheral internal wall between the top opening and the lower cavity area. An outer radial edge portion of the membrane 460 and the upper member 466 can be situated in the circumferential groove 482 such that the membrane 460 and upper member 466 are secured within the cavity 476. The base member 468 can define a plurality of ports or through holes 484 within the circumferential groove 482. The through holes 484 can allow fluid to be expelled from the pump mechanism 456 to atmosphere.

The lower cavity area can include a closure-assist mechanism comprising a plurality of resilient elements 486 defining peaks and valleys or a wavy profile. The resilient elements 486 can be generally concentric with varying heights. The resilient elements 486 can support a bottom of the membrane 460 within the cavity 476 and can help bias and/or move the pump mechanism 456 toward the original configuration.

For instance, when the connector 462 exerts a force on the membrane 460 in a direction away from the bottom of the upper member 466, the pump mechanism 456 moves toward the expanded configuration as the connector 462 pulls a center portion of the membrane 460 away from the bottom of the upper member 466 while the outer radial edge portion remains engaged with the upper member 466, causing deformation of the membrane 460 and an increase in the volume of the fluid chamber 470. This increase in the volume of the fluid chamber 470 can draw fluid into the pump mechanism 456 through the valve assembly 464.

The downward movement of the membrane 460 also forces the bottom 478 of the cavity 476 away from the bottom of the upper member 466, causing the resilient elements 486 to flex (e.g., the resilient elements 486 can be in compression and/or tension) and store mechanical energy.

Once the force from the connector 462 is reduced or removed from the membrane 460, the stored mechanical energy in the resilient elements 486 can bias or force the membrane back toward the bottom of the upper member 466, moving the pump mechanism 456 toward its original configuration. This forced closure decreases the volume of the fluid chamber 470, which, in turn, increases the pressure on the fluid within the fluid chamber 470 until the seal between the upper surface of the membrane 460 and the upper member 466 is broken. This allows the fluid to be expelled out of the pump mechanism 456 through the through holes 484 and/or out of the top opening of the cavity 476. The closure force of the resilient elements 486 can also help keep the membrane 460 sealed against the bottom of the upper member 466.

Because the pump mechanism 456 can expel fluid, preferably to atmosphere, without the use of a second valve assembly, the pump mechanism 456 is beneficially lighter and easier to manufacture and maintain. Further, the closure force of the resilient elements 486 can be customized based on the individual needs of the user. For instance, the resilient elements 486 can be dimensioned and/or formed of selected materials to vary the closure force.

Another embodiment is shown in FIG. 28. This embodiment can include a pump mechanism 490 similar to the previously described pump mechanism embodiments. The pump mechanism 490 includes a housing 492 containing a valve assembly 494, a membrane, and a connector. The valve assembly 494 only allows fluid to enter the pump mechanism 490 which can be in fluid communication with the cavity of a socket. An arm member 496 including a pair of bar members can be attached to the housing 492, and connected together a distance from the housing 492. Each bar can include a first portion extending from the housing 492 and a second portion curving downwardly from the first portion. The arm member 496 can engage a portion of a prosthetic foot to move the pump mechanism 490 as described herein.

The pump mechanism 490 relies upon deformation of the membrane to move between an original configuration in which the volume of a fluid chamber defined between the top surface of the membrane and the bottom of the housing 492 is zero or near-zero, and an expanded configuration in which the volume of the fluid chamber is increased. The housing 492 is arranged to surround the outer radial edge portion of the membrane and creates a seal with the membrane. The bottom surface of the housing 492 can define an opening which extends into the housing 492 to form an internal passageway to provide fluid communication between the fluid chamber and the valve assembly 494. An aperture or outlet 498 is defined in the housing 492 to provide fluid communication between the fluid chamber and preferably atmosphere.

When a force is exerted on the membrane away from the housing 492, the pump mechanism 490 moves toward the expanded configuration as the volume of the fluid chamber increases. This volume increase can draw fluid into the pump mechanism 490 through the valve assembly 494.

Once the force is reduced or removed from the membrane, the pump mechanism 490 returns toward its original configuration as the membrane returns toward the bottom of the housing 492. This closing movement decreases the volume of the fluid chamber, which, in turn, increases the pressure in the fluid chamber until the seal between the membrane and the housing 492 is broken, allowing fluid in the fluid chamber to be expelled out of the outlet 498. The pump mechanism 490 is beneficially lighter or easier to make. Similar to the other embodiments, the pump mechanism 490 can include a closure-assist mechanism arranged to help move or maintain the pump mechanism 490 in its original configuration.

While various aspects and embodiments have been disclosed herein, other aspects and embodiments are contemplated. For instance, the membrane used in the embodiments described can vary in thickness in different areas and in shape. The thickness of the membrane may be thicker at the portions attached to the rigid wall to create a stronger connection and greater deformation of the membrane wall. Similarly, the membrane wall may be thinner than the attachment portions to allow for greater displacement with less force. The membrane may be a cylindrical shape, a tapered shape, or any other suitable shape. In other embodiments, the pump mechanism can include a plurality of closure-assist mechanisms such as a magnetic closure element and a resilient closure element.

In other embodiments, the pump system can be arranged to move the pump mechanism from its original configuration to its expanded configuration upon expansion of the prosthetic foot or heel strike. In other embodiments, the pump mechanism can move from its original configuration to its expanded configuration upon heel strike and/or toe-off. It should be appreciated that embodiments of the pump system described herein can be coupled to any suitable prosthetic foot. For instance, the embodiments of the foot system can be coupled to the prosthetic foot described in U.S. patent application Ser. No. 13/309,418, filed on Dec. 1, 2011, and commercially available as the XC VARI-FLEX by Össur hf. This disclosure is incorporated by reference and belongs to the assignee of this disclosure.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic system comprising:
a prosthetic foot including an upper foot element having a concave-forward facing portion and a foot portion extending forwardly therefrom, an intermediate foot element disposed below the upper foot element and having a front portion coupled to the foot portion of the upper foot element, and a lower foot element disposed below the intermediate foot element, wherein the upper foot element and the intermediate foot element are movable relative to one another upon movement of the prosthetic foot; and
a pump system coupled to the prosthetic foot and comprising:
a pump mechanism including a housing defining a cavity and a membrane situated in the cavity, the pump mechanism being movable between an original configuration in which the volume of a fluid chamber defined between the membrane and a bottom of the cavity is zero or near-zero, and an expanded configuration in which the volume of the fluid chamber is increased; and
an arm member extending from the pump mechanism and operatively coupled to the intermediate foot element, the arm member arranged to move the pump mechanism toward at least the expanded configuration upon movement of the intermediate foot element relative to the upper foot element;
wherein the pump mechanism includes a closure-assist mechanism arranged to bias the pump mechanism toward the original configuration;
wherein the housing includes a main portion, a front portion, and a width that tapers from the main portion toward the front portion of the housing.

2. The prosthetic system of claim 1, wherein the arm member is selectively engageable with an upper surface of the intermediate foot element and has a rigid configuration.

3. The prosthetic system of claim 2, wherein the arm member comprises an elongate member defined by the housing and extending downwardly through an opening defined in the upper foot element and toward the intermediate foot element.

4. The prosthetic system of claim 3, wherein the elongate member defines a width increasing in a direction toward the intermediate foot element.

5. The prosthetic system of claim 3, wherein the elongate member defines a key arranged to fit in a corresponding keyway defined by the housing.

6. The prosthetic system of claim 1, wherein a distance between the pump mechanism and the intermediate foot element is adjustable to vary sensitivity of the pump mechanism.

7. The prosthetic system of claim 1, wherein a distance between a portion of the pump mechanism and the upper foot element is adjustable to vary sensitivity of the pump mechanism.

8. The prosthetic system of claim 1, wherein the closure-assist mechanism comprises a plurality of resilient elements defined by the housing.

9. The prosthetic system of claim 1, wherein flexion of the housing at the front portion allows the pump mechanism to move between the original configuration and the expanded configuration.

10. The prosthetic system of claim 1, further comprising:
an ankle portion rotatably attached to the upper foot element; and
a connection unit connected to a rear portion of the ankle portion and a rear end portion of the intermediate foot element, the connection unit being arranged to move the upper and intermediate foot elements relative to one another.

11. The prosthetic system of claim 10, wherein rotation of the ankle portion in a first direction causes the connection unit to pull the rear end portion of the intermediate foot element toward the upper foot element.

12. The prosthetic system of claim 11, wherein rotation of the ankle portion in a second direction causes the connection unit to force the rear end portion of the intermediate foot element away from the upper foot element.

13. The prosthetic system of claim 1, wherein the closure-assist mechanism comprises a closure element having one or more magnetic materials.

14. A pump system arranged to be connected to a prosthetic foot and a prosthetic socket, the pump system comprising:
a pump mechanism including a housing defining a cavity and a membrane situated in the cavity, the pump mechanism being movable between an original configuration in which the volume of a fluid chamber defined between the membrane and a bottom of the cavity is zero or near-zero, and an expanded configuration in which the volume of the fluid chamber is increased, the pump mechanism arranged for fluid communication with the prosthetic socket; and
an arm member extending from the pump mechanism and arranged to move the pump mechanism toward the expanded configuration upon engagement with the prosthetic foot and movement of the prosthetic foot;
wherein the pump system is arranged to be placed a distance from the prosthetic foot and said distance is adjustable to vary sensitivity of the pump mechanism;
wherein the arm member has an elongate member defined by the housing and arranged to extend downwardly toward the prosthetic foot;
wherein the pump mechanism includes a closure-assist mechanism arranged to bias the pump mechanism toward the original configuration;
wherein the closure-assist mechanism comprises a closure element having one or more magnetic materials.

15. The pump system of claim 14, wherein the elongate member defines a width increasing in a direction toward the prosthetic foot.

16. The pump system of claim 14, wherein the elongate member defines a key arranged to fit in a corresponding keyway defined by the housing.

17. A prosthetic system comprising:
a prosthetic foot including an upper foot element having a concave-forward facing portion and a foot portion extending forwardly therefrom, an intermediate foot element disposed below the upper foot element and having a front portion coupled to the foot portion of the upper foot element, and a lower foot element disposed below the intermediate foot element, wherein the upper foot element and the intermediate foot element are movable relative to one another upon movement of the prosthetic foot; and
a pump system coupled to the prosthetic foot and comprising:
a pump mechanism including a housing defining a cavity and a membrane situated in the cavity, the pump mechanism being movable between an original configuration in which the volume of a fluid chamber defined between the membrane and a bottom of the cavity is zero or near-zero, and an expanded configuration in which the volume of the fluid chamber is increased; and
an arm member extending from the pump mechanism and operatively coupled to the intermediate foot element, the arm member arranged to move the pump mechanism toward at least the expanded configuration upon movement of the intermediate foot element relative to the upper foot element;
wherein the pump mechanism includes a closure-assist mechanism arranged to bias the pump mechanism toward the original configuration;
an ankle portion rotatably attached to the upper foot element; and
a connection unit connected to a rear portion of the ankle portion and a rear end portion of the intermediate foot element, the connection unit being arranged to move the upper and intermediate foot elements relative to one another.

18. The prosthetic system of claim 17, wherein rotation of the ankle portion in a first direction causes the connection unit to pull the rear end portion of the intermediate foot element toward the upper foot element.

19. The prosthetic system of claim 18, wherein rotation of the ankle portion in a second direction causes the connection unit to force the rear end portion of the intermediate foot element away from the upper foot element.

* * * * *